US007964629B2

(12) United States Patent
Casey et al.

(10) Patent No.: US 7,964,629 B2
(45) Date of Patent: Jun. 21, 2011

(54) INHIBITORS OF ISOPRENYLCYSTEINE CARBOXYL METHYLTRANSFERASE

(75) Inventors: Patrick J. Casey, Durham, NC (US); Rudi A. Baron, Durham, NC (US); Ann M. Winter-Vann, Durham, NC (US)

(73) Assignee: Duke Universtiy, Durham, NC (US)

( * ) Notice: Subject to any disclaimer, the term of this patent is extended or adjusted under 35 U.S.C. 154(b) by 462 days.

(21) Appl. No.: 11/886,291

(22) PCT Filed: Mar. 20, 2006

(86) PCT No.: PCT/US2006/009806
§ 371 (c)(1), (2), (4) Date: Sep. 14, 2007

(87) PCT Pub. No.: WO2006/102126
PCT Pub. Date: Sep. 28, 2006

(65) Prior Publication Data

US 2008/0171782 A1 Jul. 17, 2008

Related U.S. Application Data

(60) Provisional application No. 60/662,801, filed on Mar. 18, 2005.

(51) Int. Cl.
*A61K 31/404* (2006.01)
*C12Q 1/48* (2006.01)
*C07D 209/12* (2006.01)

(52) U.S. Cl. .......................... 514/419; 435/15; 548/494

(58) Field of Classification Search ............... 548/360.1, 548/469; 514/387, 415
See application file for complete search history.

(56) References Cited

U.S. PATENT DOCUMENTS 5,578,634 A * 11/1996 Bach et al. .................... 514/419

OTHER PUBLICATIONS

Baron, R. and Casey, P. "Analysis of the kinetic mechanism of recombinant human isoprenylcysteine carboxylmethyltrasnferase (lcmt)," BMC Biochemistry (2004)5:19, pp. 1-12.*

Winter-Vann, A. et al, A small-molecule inhibitor of isoprenylcysteine carboxyl methyltransferase with antitumor activity in cancer cells, PNAS (2005), vol. 102(12), pp. 4336-4341.*

* cited by examiner

*Primary Examiner* — Rebecca L Anderson
*Assistant Examiner* — Alicia L Otton
(74) *Attorney, Agent, or Firm* — Nixon & Vanderhye P.C.

(57) ABSTRACT

The present invention relates, in general, to isoprenylcysteine carboxyl methyltransferase (Icmt) and, in particular, to inhibitors of Icmt and to methods of disease treatment using same.

13 Claims, 7 Drawing Sheets

2

5

Fig. 5. Summary of the synthesis of 2-[5-(3-methylphenyl)-1-octyl-1*H*-indol-3-yl]acetamide (Cysmethynil).

Figure 6
A.
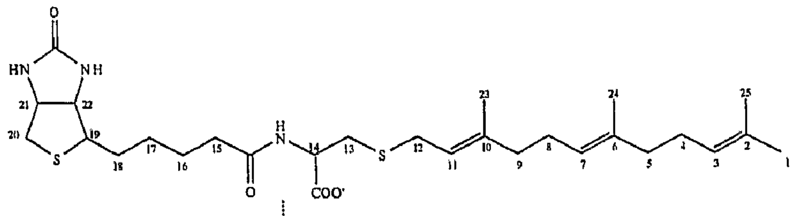
Streptavidin binding
Icmt substrate
B.
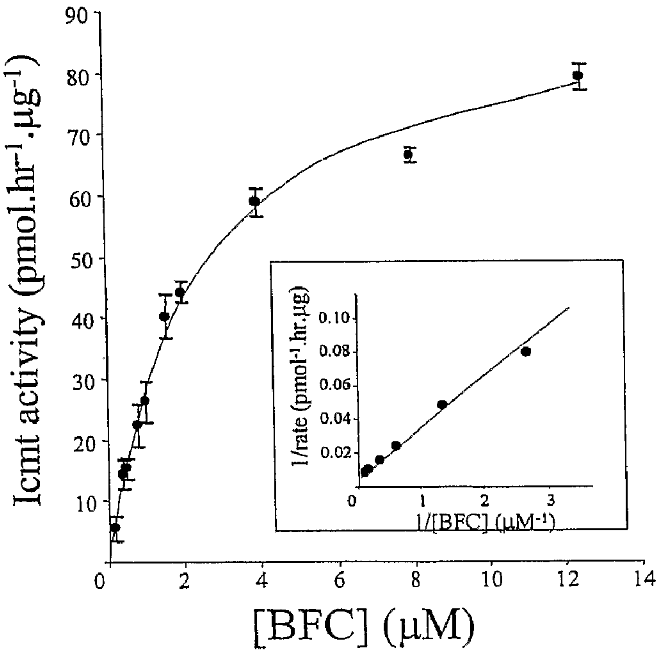

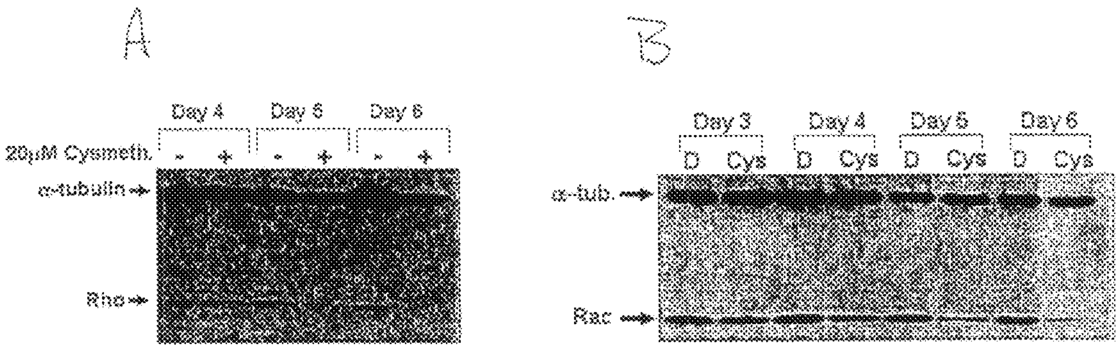
Fig. 7. Inhibition of Icmt results in reduction of steady state levels of both Rho and Rac GTPases in MDA-MB-231 breast cancer cells.

INHIBITORS OF ISOPRENYLCYSTEINE CARBOXYL METHYLTRANSFERASE

This application is the U.S. national phase of International Application No. PCT/US2006/009806, filed 20 Mar. 2006, which designated the U.S. and claims priority to U.S. Provisional Application No. 60/662,801, filed 18 Mar. 2005, the entire contents of each of which are hereby incorporated by reference.

This application claims priority from U.S. Provisional Application No. 60/662,801, filed Mar. 18, 2005, the entire content of which is incorporated herein by reference.

TECHNICAL FIELD

The present invention relates, in general, to isoprenylcysteine carboxyl methyltransferase (Icmt) and, in particular, to inhibitors of Icmt and to methods of disease treatment using same.

BACKGROUND

A C-terminal CaaX motif, where C is cysteine, the a's are aliphatic amino acids, and X can be any of a number of amino acids, targets a variety of eukaryotic proteins to a series of post-translational modifications important for their localization and function (Zhang and Casey, Annu. Rev. Biochem. 65:241-269 (1996), Kloog and Cox, Semin. Cancer Biol. 14:253-261 (2004)). This processing is initiated by the covalent attachment of a 15-carbon farnesyl or a 20-carbon geranylgeranyl lipid to the cysteine of the CaaX motif, a reaction catalyzed by protein farnesyltransferase (FTase) or protein geranylgeranyltransferase type I (GGTase-I) (Casey and Seabra, J. Biol. Chem. 271:5289-5292 (1996)). Following prenylation, the C-terminal three amino acids (i.e., the -aaX) are removed by a specific endoprotease termed Rce1 (Boyartchuk et al, Science 275:1796-1800 (1997), Otto et al, J. Biol. Chem. 274:8379-8382 (1999)) and the now C-terminal prenylcysteine moiety is methylated by the enzyme isoprenylcysteine carboxyl methyltransferase (Icmt) (Clarke et al, Proc. Natl. Acad. Sci. USA 85:4643-4637 (1988), Hrycyna et al, EMBO J. 10:1699-1709 (1991), Dai et al, J. Biol. Chem. 273:15030-15034 (1998)). As polytopic membrane proteins that are localized to the endoplasmic reticulum, both Rce1 and Icmt are unusual in their respective classes (Young et al, The Enzymes 21:156-213 (2000)).

Proteins that terminate in a -CaaX motif regulate a number of cellular pathways important in oncogenesis. The best studied example is the central role of the Ras family of CaaX proteins in growth factor activation of the Raf/mitogen-activated protein kinase (MAPK) signaling cascade (Malumbres and Barbacid, Nat. Rev. Cancer 3:459-465 (2003), Shields et al, Trends Cell Biol. 10:147-154 (2000)). Constitutive activation of this pathway is transforming in a wide variety of cell types, and activating mutations in Ras have been found in almost 30% of all cancers, including 50% of colon cancers and up to 90% of pancreatic cancers (Bos, Cancer Res. 49:4682-4689 (1989)). In addition, many cancers contain alterations in elements upstream of Ras in signaling cascades, such as amplified expression or mutational activation of tyrosine kinases, and the resultant hyperactivation of Ras is thought to contribute to tumorigenesis in these cancers as well (Gschwind et al, Nat. Rev. Cancer 4:361-370 (2004), Schlessinger, Cell 103:211-225 (2000)). In addition to Ras, many other CaaX proteins have been implicated in oncogenesis and tumor progression, and these proteins also most likely require processing via the prenylation pathway for function (Kloog and Cox, Semin. Cancer Biol. 14:253-261 (2004), Doll et al, Curr. Opin. Drug. Discov. Devel. 7:478-486 (2004)).

Both the membrane targeting and the transforming abilities of Ras require processing through the prenylation pathway (Hancock et al, Cell. 57:1167-1177 (1989), Kato et al, Proc. Natl. Acad. Sci. USA 89:6403-6407 (1992)). For this reason, the protein prenyltransferases, most notably FTase, have been targets of major drug discovery programs for the last decade (Gibbs et al, Cell 77:175-178 (1994), Karp et al, Curr. Opin. Oncol. 13:470-476 (2001)). Presently, several FTase inhibitors (FTIs) are being evaluated in clinical trials (Doll et al, Curr. Opin. Drug. Discov. Devel. 7:478-486 (2004), Karp et al, Curr. Opin. Oncol. 13:470-476 (2001)). While these experimental agents have shown significant activity in a number of clinical trials, the overall response rates in patients have been less than initially hoped. One possible explanation for this lack of efficacy is the process of alternate prenylation that allows some FTase substrates to be modified by GGTase-I when FTase activity is limiting (James et al, J. Biol. Chem. 270:6221-6226 (1995), Whyte et al, J. Biol. Chem. 272:14459-14464 (1997), Sebti and Der, Nat. Rev. Cancer 3:945-951 (2003)). Recent studies using genetic disruption of Icmt have demonstrated that Ras proteins, including K-Ras, are significantly mislocalized and tumorigenesis is markedly impaired in cells that lack Icmt (Bergo et al, J. Clin. Invest. 113:539-550 (2004), Bergo et al, J. Biol. Chem. 275:17605-17610 (2000)). Following this discovery, CaaX protein methylation has gained attention as a new target in oncogenesis (Clarke and Tamanoi, J. Clin. Invest. 113:513-515 (2004)).

With emerging evidence for the importance of Icmt-catalyzed CaaX protein methylation in oncogenesis, there is a clear need for specific pharmacological agents to target this process. However, the only such agents available to date have been analogs of the substrate prenylcysteine or the product S-adenosylhomocysteine; all of these have been reported to have pleiotropic effects on cells (Chiang et al, FASEB J. 10:471-480 (1996), Ma et al, Biochemistry 33:5414-5420 (1994), Scheer and Gierschik, FEBS Lett. 319:110-114 (1993)). (See also Winter-Van and Casey, Nature Rev. Cancer 5:405-412 (2005).)

The present invention results, at least in part, from the discovery of a novel, indole-based small-molecule inhibitor of Icmt. Treatment of cancer cells with this compound, designated cysmethynil, results in a decrease in Ras carboxylmethylation, mislocalization of Ras, and impaired signaling through Ras pathways. The invention provides methods of treating diseases or disorders dependent on activity of Icmt substrates, and, more specifically, diseases or disorders associated with aberrant activity of Icmt substrates (e.g., cancer) using this and other Icmt inhibitors.

SUMMARY OF THE INVENTION

The present invention relates generally to Icmt. More specifically, the invention relates to inhibitors of Icmt, to compositions comprising such inhibitors and to methods of using inhibitors of Icmt to treat diseases/disorders associated with Icmt activity, such as cancer.

Objects and advantages of the present invention will be clear from the description that follows.

BRIEF DESCRIPTION OF THE DRAWINGS

FIG. 1A. Structure of the indole-based compound, cysmethynil. FIG. 1B. Time dependent inhibition of Icmt by cysmethynil. Icmt activity was measured as the incorporation of [$^3$H] from [$^3$H]AdoMet into the Icmt substrate BFC. The assay was performed either with (○) or without (●) preincubating Icmt with cysmethynil.

(FIG. 2A) Icmt$^{+/+}$ cells; (FIG. 2B) Icmt$^{-/-}$ cells; (C) Icmt$^{-/-}$ cells stably transfected with a gene expressing human ICMT (Icmt$^{-/-}$/ICMT cells).

FIG. 3A. Mislocalization of GFP Ras in cysmethynil treated cells. MDCK cells expressing GFP-tagged K-Ras (panels 1-4) or Yes-GFP (panels 5-8) were treated with 1% DMSO (panels 1, 5) or 10 μM (panels 2, 6), 20 μM (panels 3, 7) or 30 μM (panels 4, 8) cysmethynil. Live cells were imaged on a spinning disk confocal microscope. FIG. 3B. Impact of cysmethynil treatment on EGF-stimulated protein phosphorylation. Wild-type mouse embryonic fibroblasts were grown for three days in media containing 1% serum in the presence of DMSO or 1 μm cysmethynil. Where indicated, cells were treated with EGF for the final 10 min prior to harvesting. Cell lysates containing equal amounts of protein were resolved on a 13% SDS-polyacrylamide gel and probed with antiphospho-Akt, antiphospho-p42/44 MAPK or anti-β-tubulin antibody as indicated.

FIG. 4A. Creation of cell lines stably overexpressing Icmt. DKOB8 cells were engineered to stably express either GFP alone or a GFP-Icmt fusion protein. Membrane fractions from GFP and GFP-ICMT expressing lines were assayed for Icmt activity using the BFC assay. FIG. 4B. Overexpression of Icmt restores EGF-stimulated MAPK activation in cysmethynil-treated cells. DKOB8 cells stably expressing GFP or GFP-ICMT were either left untreated or treated with 5 μM cysmethynil for three days in reduced-serum media. Where indicated, cells were treated with EGF for the final 10 min prior to harvesting. Cell lysates containing equal amounts of protein were resolved on a 13% SDS-polyacrylamide gel and probed with antiphospho-p42/44 MAPK or, as a control, antiphospho NFκB antibody as indicated. FIG. 4C. Impact of cysmethynil on anchorage-independent growth of DKOB8 colon cancer cells. DKOB8 cells stably expressing GFP (top row) or GFP-ICMT (bottom row) were suspended in 0.3% noble agar and plated on a base of 0.6% noble agar; both the top and bottom layers contained either 1% DMSO or 10 or 20 μM cysmethynil as indicated. After 3 weeks of growth, colonies were stained with MTT and imaged.

FIGS. 6A and 6B. A new small-molecule substrate of Icmt. FIG. 6A. Structure of biotin-S-farnesyl-L-cysteine (BFC). FIG. 6B. Utilization of BFC as a substrate by recombinant human Icmt. Shown are Michaelis-Menten and Lineweaver-Burk plot (inset) of the formation of BFC-[$^3$H]methylester as a function of BFC concentration. The data shown are the mean of duplicate determinations from a single experiment and are representative of two additional experiments.

FIGS. 7A and 7B. Inhibition of Icmt results in reduction of steady state levels of both Rho (FIG. 7A) and Rac (FIG. 7B) GTPases in MDA-MB-231 breast cancer cells.

DETAILED DESCRIPTION OF THE INVENTION

Figure 1:
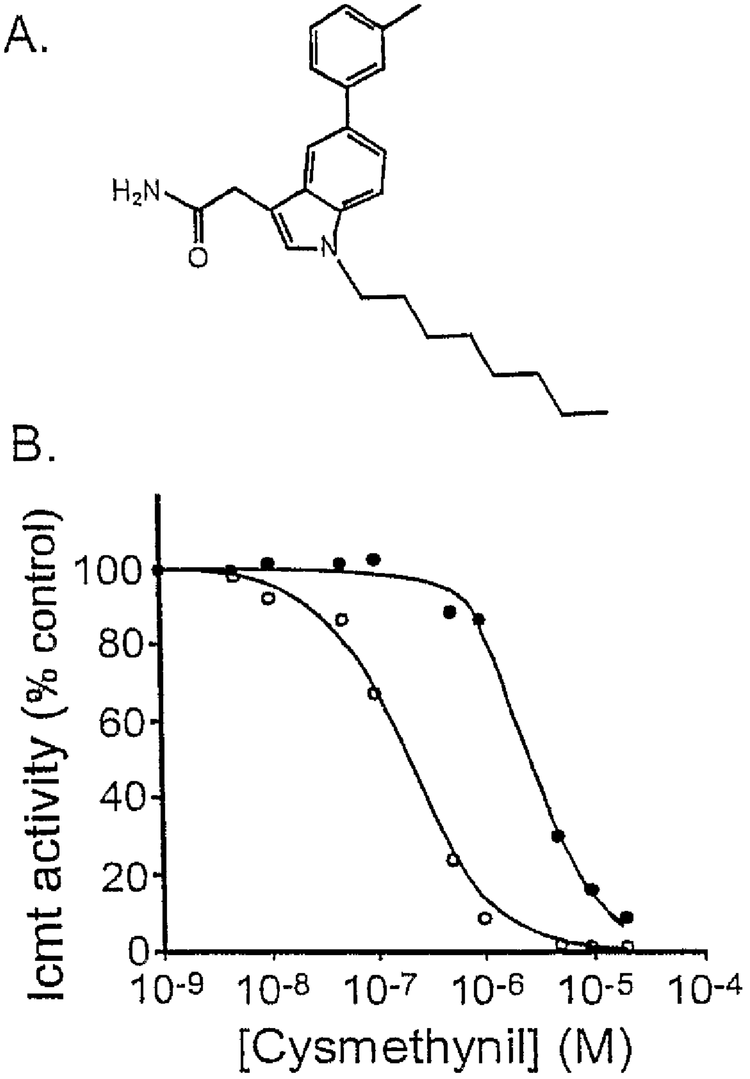
FIGS. 1A and 1B. Cysmethynil, a small molecule inhibitor of Icmt.

The present invention relates to inhibitors of Icmt, and to methods of using such inhibitors in the treatment of diseases or disorders associated with Icmt activity (e.g., disease or disorders associated with aberrant activity of Icmt substrates), such as cancer, inflammatory disorders and certain viral diseases (e.g., hepatitis C and D). The invention further relates to compositions comprising Icmt inhibitors. Inhibitors of the invention include small molecule inhibitors of Icmt that inhibit cell growth in an Icmt-dependent fashion. Advantageously, the instant inhibitors are selective in that they do not inhibit other enzymes of the prenylation pathway (e.g., FTase, GGTase, Rce1 protease) and/or AdoMet-dependent DNA methyltransferase. Inhibitors of the invention can result in mislocalization of Ras, while not globally disrupting trafficking to the plasma membrane, and can impair signaling through Ras.

Inhibitors of the invention can have structures based on an indole scaffold. Suitable inhibitors are of Formula I, or pharmaceutically acceptable salts thereof:

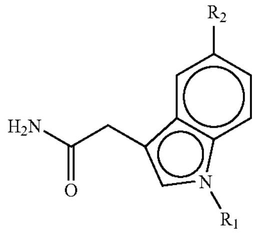

wherein $R_1$ is:

- an alkyl, (preferably, a $C_1$-$C_{20}$ alkyl, substituted (e.g., with a cycloalkyl) or unsubstituted, more preferably, a linear, branched or cyclic $C_4$-$C_{15}$ alkyl),
- a $(CH_2)_n$-substituted or unsubstituted aryl (e.g., a $(CH_2)_n$-phenyl or $(CH_2)_n$-napthyl, preferably, a $(CH_2)_n$-phenyl wherein said phenyl is unsubstituted or meta or para substituted with at least one unsubstituted or substituted alkyl (e.g., a $C_1$-$C_6$ alkyl, preferably, a $C_1$-$C_4$ alkyl, more preferably, a branched $C_4$ unsubstituted alkyl or a $CX_3$, wherein at least one X is a halogen), n being an integer between 0 and 6, preferably, between 1 and 4, more preferably, 1 or 2, or
- a $(CH_2)_n$—O-substituted or unsubstituted aryl (e.g., a $(CH_2)_n$—O-phenyl or $(CH_2)_n$—O-napthyl, preferably, a $(CH_2)_n$—O-phenyl wherein said phenyl is unsubstituted or meta or para substituted with at least one unsubstituted or substituted alkyl (e.g., a $C_1$-$C_6$ alkyl, preferably, a $C_1$-$C_4$ alkyl, more preferably, a branched $C_4$ unsubstituted alkyl or a $CX_3$, wherein at least one X is a halogen), n being an integer between, 0 and 6, preferably, between 1 and 4, more preferably, 1 or 2; and where $R_2$ is:

- a $(CH_2)_m$-substituted or unsubstituted aryl (e.g., a $(CH_2)_m$-phenyl), preferably, a $(CH_2)_m$-phenyl wherein said phenyl is unsubstituted or substituted with at least one halogen, at least one unsubstituted or substituted alkyl (e.g., a $C_1$-$C_6$ alkyl, preferably, a $C_1$-$C_4$ alkyl, more preferably, $CX_3$, wherein at least one X is a halogen), or at least one —O—Y wherein Y is a $C_1$-$C_4$ alkyl or an aryl (preferably phenyl, substituted or unsubstituted), m being an integer between 0 and 4, preferably 0 or 1.

Specific inhibitors of the indole type are set forth in Tables 1 and 2:

TABLE 1

| | | $IC_{50}$ | |
|---|---|---|---|
| | | Scaffolds | |
| $R_1$ | 1: 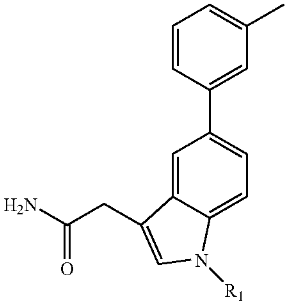 | 2: 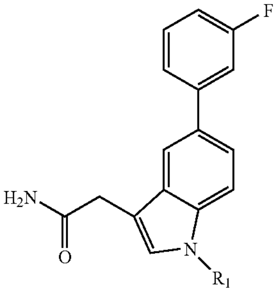 | 3: 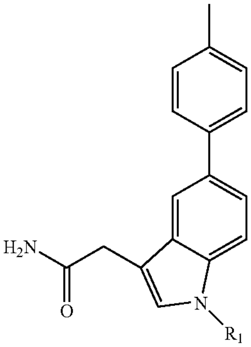 |
| ($a_1$) 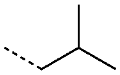 | 15.7 ± 2 μM | 13.7 ± 0.3 μM | 9.8 ± 5.7 μM |
| ($b_1$) 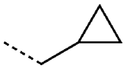 | 9.1 ± 1.8 μM | 14.8 ± 5.3 μM | 11.3 ± 0.6 μM |
| ($c_1$) 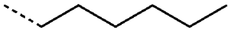 | 7.4 ± 0.4 μM | 12.8 ± 0.7 μM | 7.33 ± 1.34 μM |
| ($d_1$) 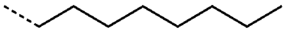 | 2.1 ± 0.9 μM | 2.4 ± 1.2 μM | 10.6 ± 2.7 μM |
| ($e_1$) 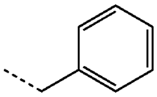 | 6.4 ± 2 μM | 10.8 ± 2 μM | — |
| ($f_1$) 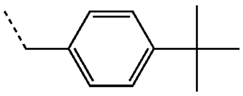 | — | 5 ± 1.1 μM | — |
| ($g_1$) 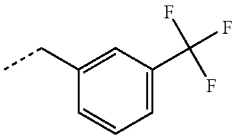 | 8 ± 4.5 μM | 5.7 ± 4.5 μM | 6.4 ± 0.5 μM |
| ($h_1$) 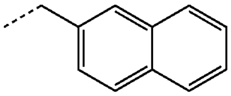 | 17.2 ± 4.3 μM | — | 19.3 ± 4.2 μM |

TABLE 2
| Compound/ Ref. | Structure | IC50 (μM) | IC50 pre-inc (μM) |
|---|---|---|---|
| 9L8/ A119041 | 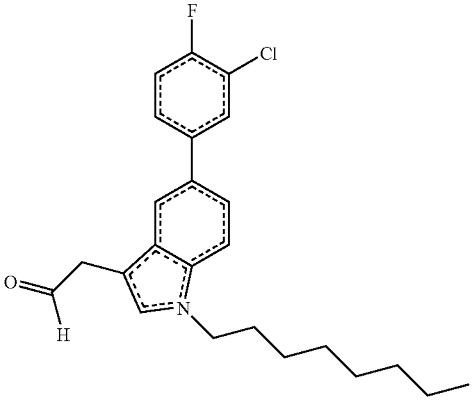 | 1 | |
| 9F20/ A119046 | 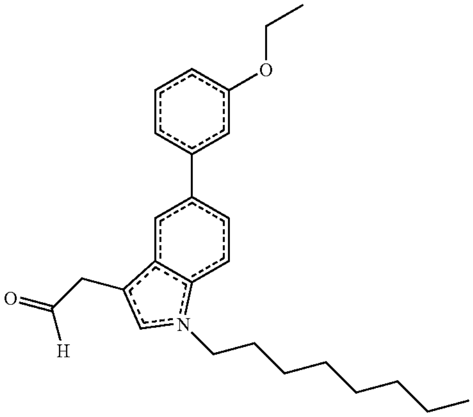 | 2 | |
| 9J20/ A119044 | 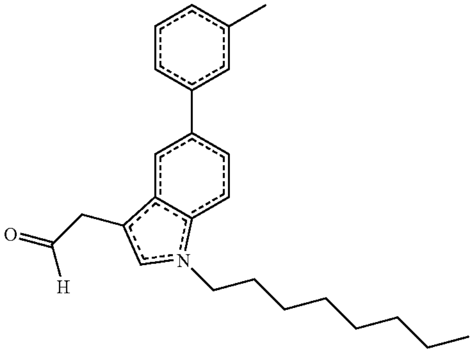 | 3 | <0.3 |
| 9J18/ A119045 | 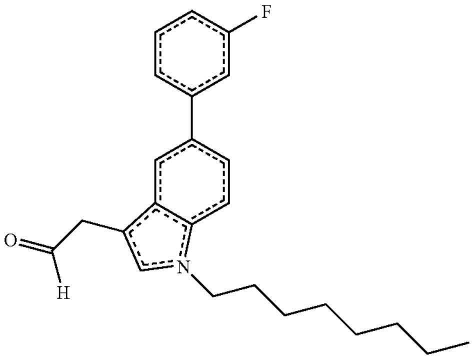 | 3 | <0.3 |

TABLE 2-continued
| Compound/ Ref. | Structure | IC50 (μM) | IC50 pre-inc (μM) |
|---|---|---|---|
| 9B6/ A119030 | 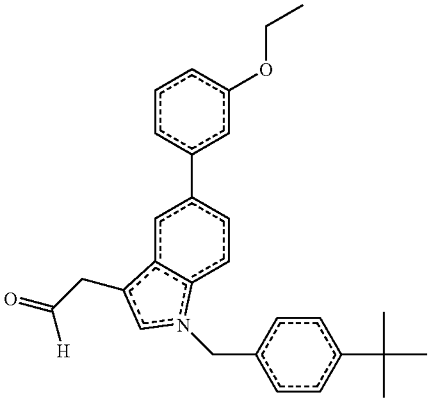 | 3 | |
| 9B4/ A119024 | 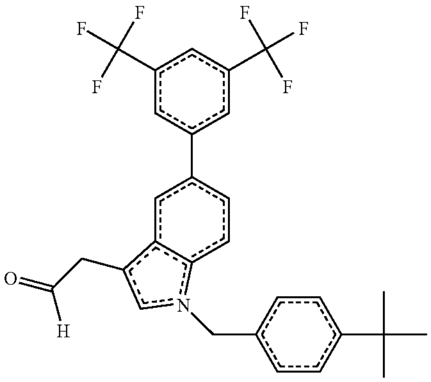 | 4 | |
| 9B12/ A119029 | 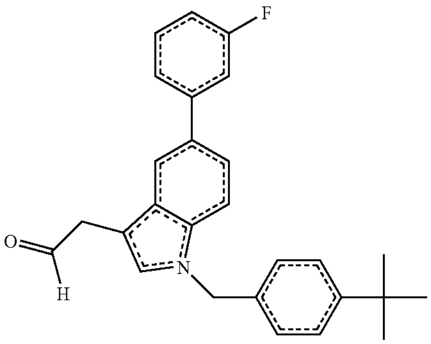 | 4 | |
| 9J16/ A119043 | 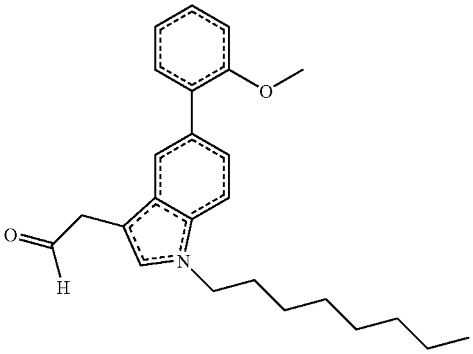 | 5 | |

TABLE 2-continued
| Compound/ Ref. | Structure | IC50 (μM) | IC50 pre-inc (μM) |
|---|---|---|---|
| 9D18/ A119047 | 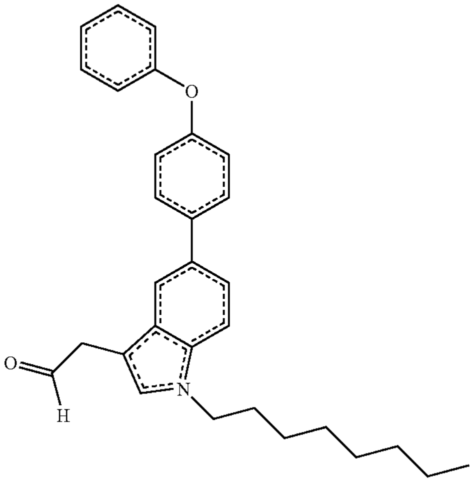 | 5 | |
| 9N6/ A119025 | 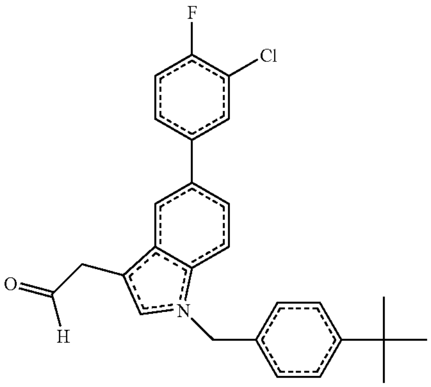 | 5 | |
| 9F10/ A119038 | 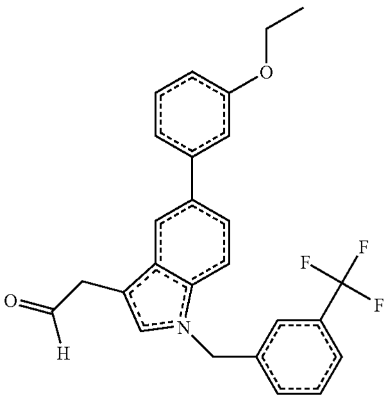 | 6 | |

TABLE 2-continued
| Compound/ Ref. | Structure | IC50 (μM) | IC50 pre-inc (μM) |
| --- | --- | --- | --- |
| 9H14/ A119033 | 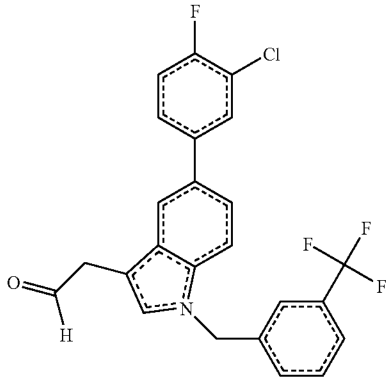 | 6 | |
| 9B8/ A119007 | 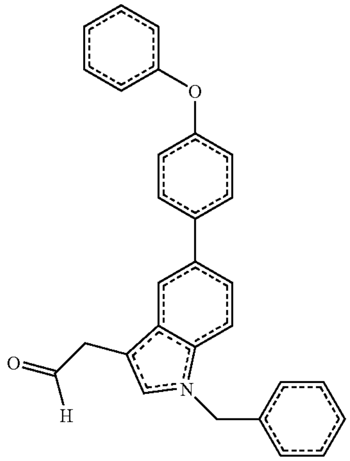 | 7 | |
| 9D12/ A119039 | 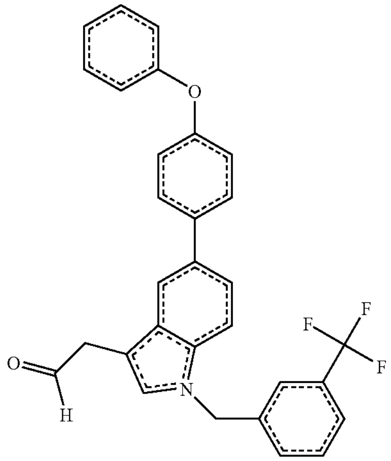 | 7 | |

TABLE 2-continued
| Compound/ Ref. | Structure | IC50 (μM) | IC50 pre-inc (μM) |
|---|---|---|---|
| 9H10/ A119022 | 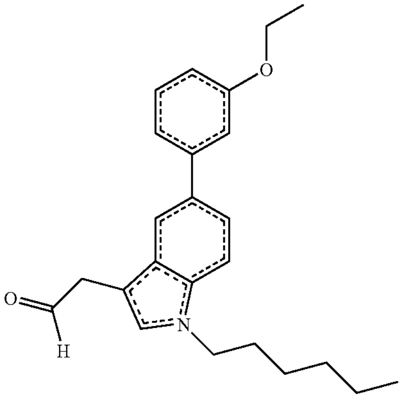 | 7 | |
| 9F18/ A119017 | 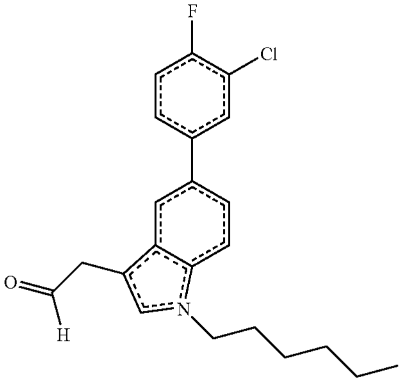 | 7 | |
| 9J22/ A119020 | 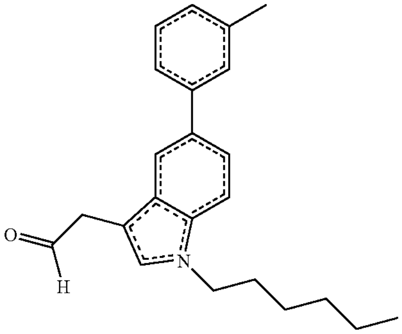 | 7 | |
| 9H4/ A119034 | 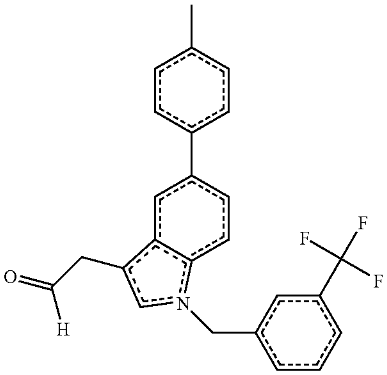 | 7 | |

TABLE 2-continued
| Compound/ Ref. | Structure | IC50 (μM) | IC50 pre-inc (μM) |
|---|---|---|---|
| 9B22/ A119064 | 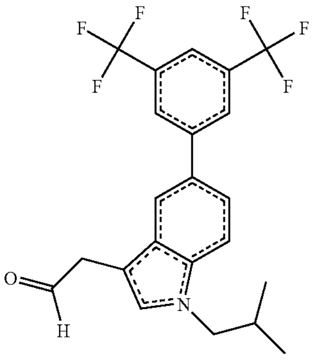 | 8 | |
| 9N10/ A119001 | 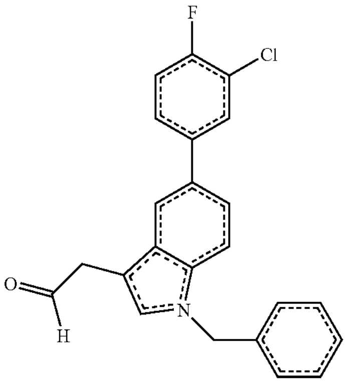 | 9 | |
| 9L6/ A119042 | 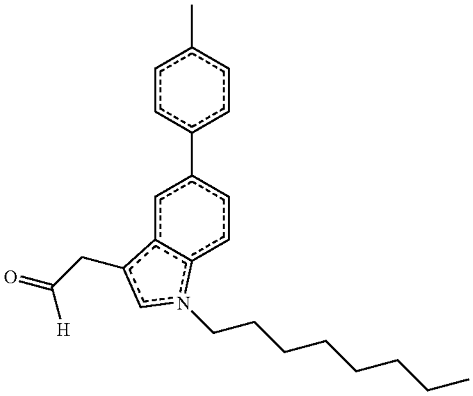 | 9 | |

TABLE 2-continued
| Compound/ Ref. | Structure | IC50 (μM) | IC50 pre-inc (μM) |
|---|---|---|---|
| 9B20/ A119055 | 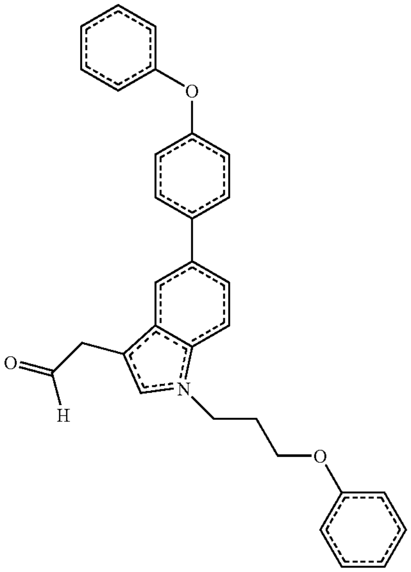 | 14 | |
| 9H6/ A119000 | 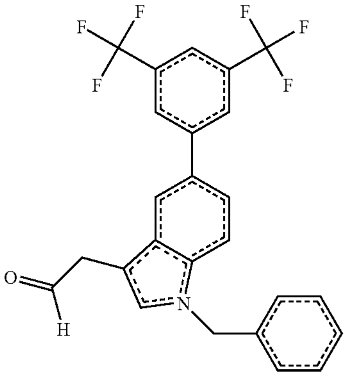 | 18 | |
| 9N12/ A119075 | 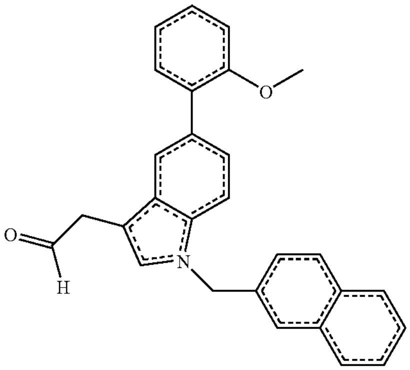 | 18 | |

TABLE 2-continued
| Compound/ Ref. | Structure | IC50 (μM) | IC50 pre-inc (μM) |
|---|---|---|---|
| 9D20/ A110023 | 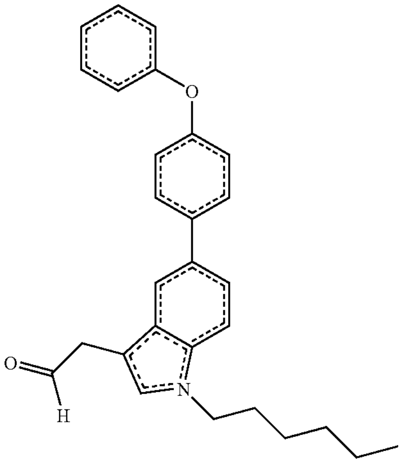 | 20 | |
| 9N14/ A119079 | 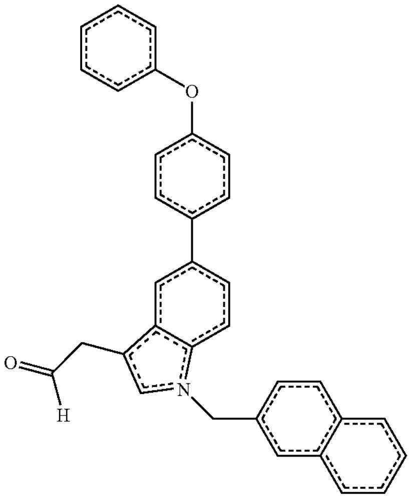 | 20 | |
| 9N22/ A119076 | 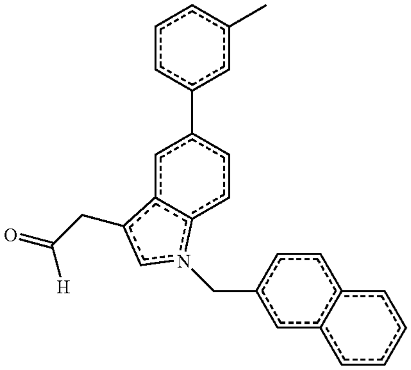 | 20 | |

TABLE 2-continued
| Compound/ Ref. | Structure | IC50 (μM) | IC50 pre-inc (μM) |
|---|---|---|---|
| 9H12/ A119056 | 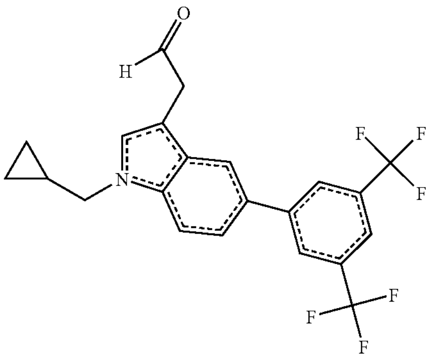 | 20 | |
| 9L4/ A119018 | 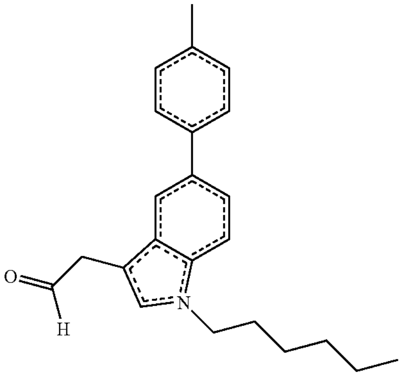 | 23 | |
| 9J8/ A119057 | 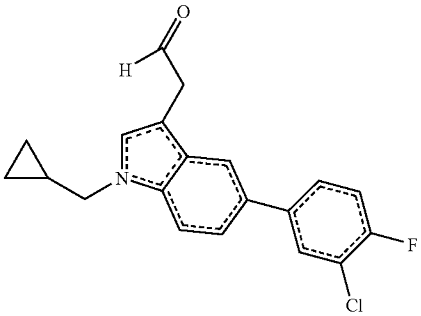 | >30 | |
| 9N8/ A119058 | 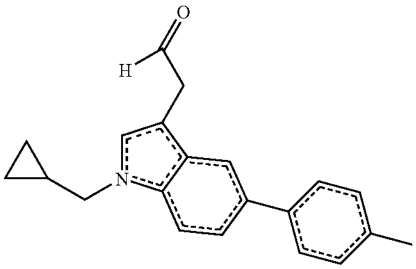 | >30 | |

TABLE 2-continued
| Compound/ Ref. | Structure | IC50 (μM) | IC50 pre-inc (μM) |
|---|---|---|---|
| 9F8/ A119059 | 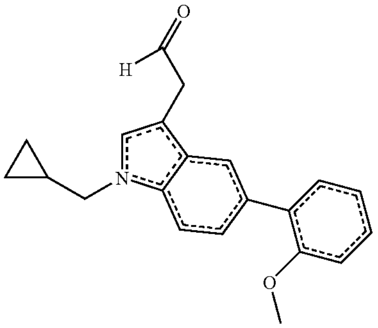 | >30 | |
| 9L10/ A119032 | 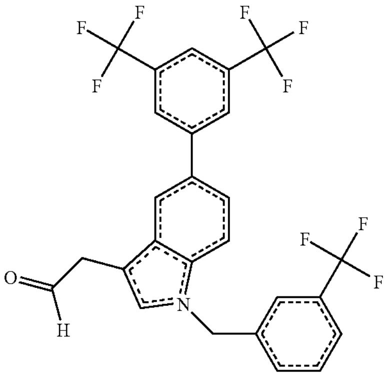 | >30 | |
| 9D10/ A119048 | 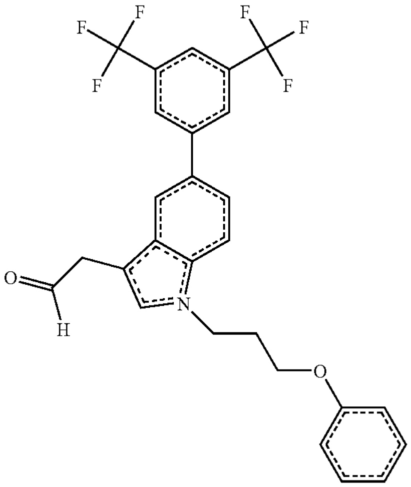 | >30 | |
| 9H20/ A110019 | 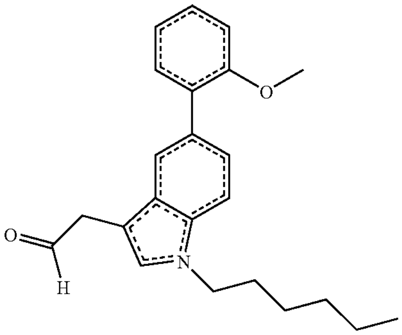 | >30 | |

TABLE 2-continued

| Compound/ Ref. | Structure | IC50 (μM) | IC50 pre-inc (μM) |
|---|---|---|---|
| 9L22/ A119040 | 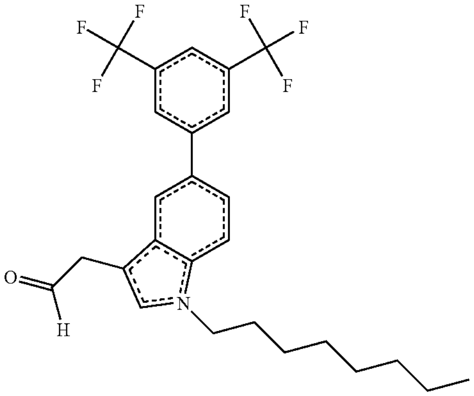 | >30 | |

1The structures of compounds provided under specific reference numbers were confirmed by LC/MS when the combinatorial library was produced. The only structure confirmed subsequently by resynthesis was that of the compound of reference number 9J20/A119044.

Preferred inhibitors are those having an $IC_{50}$ of less than about 20 μM more preferably less than about 5 μM or, still more preferably, less than about 1 μM. Certain of the inhibitors of the invention exhibit a phenomenon known as time-dependent inhibition, meaning that pre-incubation of the enzyme with the inhibitor results in formation of a high affinity complex. This is manifest as a reduction in the $IC_{50}$. (See Example 4.)

The inhibitors of the invention, or pharmaceutically acceptable salts thereof, can be synthesized using art-recognized techniques and readily available starting materials. By way of example, the synthesis of cysmethynil is set forth below.

The inhibitors of the invention can be used to treat human and non-human mammals suspected of having or being prone to a disease, disorder or condition associated with expression of Icmt by administering a therapeutically or prophylactically effective amount of one or more of the inhibitors of the invention. One such disease is cancer. Cancer types particularly amenable to treatment using the present inhibitors include colo-rectal cancer, pancreatic cancer, breast cancer, lung cancer, cancer of the head and neck and certain leukemias. Chronic inflammatory disorders, including multiple sclerosis and rheumatoid arthritis, are also amenable to treatment using the present inhibitors, or as are osteoporosis, stroke, asthma and glaucoma.

The inhibitors of the invention can be formulated into compositions, for example, pharmaceutical compositions, suitable for administration by, for example, oral, parenteral (including intravenous, intraarterial, intramuscular, subcutaneous, and intraperitoneal), intracranial or topical routes. Such compositions can include the inhibitor together with a carrier (e.g., a pharmaceutically acceptable carrier), excipient or diluent. The composition can be present in dosage unit form, for example, a tablet, capsule or suppository. The composition can also be in the form of a sterile solution suitable for injection or nebulization. The compositions can also be in a form suitable for opthalmic use. The invention further includes compositions formulated for topical administration, such compositions taking the form, for example, of a lotion, cream, gel or ointment. The concentration of inhibitor to be included in the composition can be selected based on the nature of the inhibitor, the dosage regimen and the result sought.

The optimum dosage of the composition of the invention to be administered can be determined without undue experimentation and will be dependent upon various factors including the nature of the inhibitor, the route of administration, the patient, and the result sought to be achieved. A suitable dosage of inhibitor to be administered IV or topically can be expected to be in the range of about 2 μM to 20 μM, preferably, 10 μM to 20 μM. For aerosol administration, doses can be used that result in a concentration at the target site of, for example, about 10-20 μM. Suitable doses of inhibitor can vary, for example, with the inhibitor the mode of administration and with the result sought.

Certain aspects of the invention are described in greater detail in the non-limiting Examples that follows.

Example 1

A Small Molecule Inhibitor of Icmt with Antitumor Activity

Experimental Details

Materials

Multiscreen plates for screening were purchased from Millipore. Farnesyl pyrophosphate was purchased from Biomol, the chemical library was purchased from PPD Discovery (Research Triangle Park, N.C.), streptavidin-sepharose beads were purchased from Amersham, puromycin and AdoMet were obtained from Sigma, and AdoHcy was from Fluka. Epidermal growth factor was from EMD Bioscience. [H-methyl]-methionine and [$^3$H-methyl]AdoMet were from PerkinElmer. CellTiter 96 AqueousOne Solution cell proliferation assay was from Promega (Madison, Wis.). pEGFP and pLPCX were from Clontech (Palo Alto, Calif.). Sf9 membranes containing recombinant Rce1 and Icmt were produced as described (Otto et al, J. Biol. Chem. 274:8379-8382 (1999)). Farnesylated K-Ras was produced by in vitro modification of bacterially-expressed K-Ras with purified FTase as described (Otto et al, J. Biol. Chem. 274:8379-8382 (1999)). Biotin-5-farnesyl-L-cysteine (BFC) was synthesized as detailed in Example 3. MDCK cells stably expressing GFP- H-Ras, GFP-K-Ras and GFP-N-Ras were a generous gift of M. Philips (NYU Medical School, New York, N.Y.)

Icmt Assay: Screening Method

The small molecule screen was performed in 96-well plates using a Beckman Biomek FX robot. Briefly, Sf9 membranes containing Rce1 and Icmt were suspended in 100 mM Hepes, pH 7.4, 5 mM $MgCl_2$ (Buffer A) such that 40 µl of suspension contained 1 µg of Rce1 membrane protein and 0.2 µg of Icmt membrane protein. This 40 µl of membrane suspension was dispensed into the wells of the plates, to which was added the library compounds in DMSO (1.3 µl) to yield a final concentration of compound in the well of 15-30 µM. After fifteen min at room temperature, 10 µl of Buffer A containing 13 µM [$^3$H]AdoMet (5 Ci/mmol) and 5 µM farnesylated K-Ras were added. Following a 30 min incubation, the reaction was quenched by addition of 100 µl of 6% SDS/45% TCA. Precipitated proteins were trapped on the plates by filtration, and the plates were then washed 3 times with 200 µl of 6% TCA in each well. Scintillation fluid (50 µl per well) was added and radioactivity in each well determined using a Packard TopCount instrument.

Icmt Assay: Secondary Analysis Method

Secondary assays and kinetic analysis of Icmt inhibitors was performed using a manual assay. These reactions were initiated by adding recombinant Icmt (0.5 µg of Sf9 membrane protein) to an assay mixture containing 4 µM BFC, 5 µM [$^3$H]AdoMet (1.2 Ci/mmol) and either inhibitor or DMSO in a total volume of 45 µl of Buffer A. Reactions were incubated for 20 min at 37° C., terminated by addition of 5 µl of 10% Tween 20, and then 10 µl of streptavidin beads previously suspended in 500 µl 20 mM $NaH_2PO_4$, pH 7.4, 150 mM NaCl (Buffer B) was added. The interaction between biotin and streptavidin was allowed to proceed overnight at 4° C. under gentle agitation, whereupon the beads were harvested by centrifugation, washed 3 times with 0.5 ml of Buffer B, and then resuspended in 100 µl of the same buffer for radioactivity determination. In the experiments designed to measure potential time-dependent inhibition of Icmt, the same assay was employed except that the resuspended Icmt membrane suspension was first mixed with the inhibitor in Buffer A in a total volume of 40 µl; this solution was incubated for 30 minutes at 37° C. whereupon the remaining components of the reaction mixture were added and the reactions incubated an additional 20 min at 37° C. prior to product isolation and radioactivity determination as above.

Cell Growth Determination

Cell growth assays were performed in a 96-well plate format. Briefly, 500 to 1000 cells were plated into 96-well plates. After the cells were allowed to attach for 24 h, media was removed and replaced with media containing either compound or vehicle. Media and drug were replaced every 24 h throughout the assay. Cell determinations were made at the times indicated in the respective figure by adding 19 µl of CellTiter 96 AqueousOne solution to each well followed by incubation of the plates in the dark at 37° C. for two hr after which the absorbance at 490 nm was read. Background absorbance from blank wells containing only media with compound or vehicle was subtracted from each test well. Typically, 3-6 replicate wells were employed for each point in each assay.

Localization of GFP Proteins in MDCK Cells

MDCK cells stably expressing GFP-H-Ras, GFP-K-Ras or GFP-N-Ras were grown on 35 mm coverslip dishes (MatTek Corporation, Ashland, Mass.) treated with poly-D-lysine. MDCK cells expressing YesGFP were prepared by transient transfection of the Yes-GFP construct (McCabe and Berthiaume, Mol Cell Biol 10:3771-3786 (1999)) using Superfect reagent (Quiagen, Valencia, Calif.) following the manufacturer's instructions. Cells were grown in media containing 10% FBS to approximately 25% confluence and then treated with 1% DMSO or cysmethynil at the indicated concentrations. Cells were imaged 72 h after drug treatment (24 h for transiently transfected cells) on an Olympus IX70 inverted microscope (Melville, N.Y.) with an UltraView spinning-disk confocal (PerkinElmer LAS, Wellesley, Mass.) and a Krypton/Argon laser, 488 nm line, attached to a cooled-CCD camera (Hamamatsu, Bridgewater, N.J.). Initial image acquisition and manipulation was done on MetaMorph image acquisition software (Universal Imaging Corp., Downington, Pa.).

Phosphoprotein Analysis:

Cells were grown in media containing 1% FBS, in the presence of cysmethynil or vehicle as indicated in the appropriate figure legend, for three days. Half of the wells were then treated with EGF (10 ng/ml) and half with vehicle for 10 min. Cells were rinsed with PBS and harvested in SDS-PAGE loading buffer. Total cell lysates (30 µg protein) were resolved on 4-20% Tris-glycine polyacrylamide gels (Invitrogen). Proteins were transferred to nitrocellulose and probed with a mix of anti-phospho-Akt and anti-phospho-p42/44 MAPK antibodies, or with anti-tubulin or anti-phospho NFκB antibody (Cell Signaling Technology) as indicated. Visualization was performed with alkaline phosphatase (Promega, Madison, Wis.) as per the manufacturer's instructions.

Generation of Stable Cell Lines Expressing GFP or GFP-Icmt

Full-length human ICMT was cloned into pEGFP following restriction endonuclease digestion with BamHI and XhoI. Retroviral constructs were generated by cloning EGFP or GFP-ICMT into the pLPCX retroviral vector. These constructs, along with the helper plasmid 467 (a gift from C. Counter, Duke University), were transfected into BEK293 cells. Virus was harvested 48 h after transfection and used to infect DKOB8 cells. Cells were treated with virus for 24 hr, allowed to recover for another 24 hr, selected in 0.5 µg per ml puromycin for approximately three weeks, and then sorted for expression of GFP on a Becton Dickinson FACSVantageSE cell sorter. GFP positive cells selected in this manner were cultured as per normal DKOB8 cells (Habets et al, Methods Enzymol. 332:245-260 (2001)).

Soft Agar Growth Assay

Soft agar culture media was prepared with 10% FBS in 1× minimum essential medium (MEM) alpha. Bottom agar (0.5 ml 2.4% noble agar in 1.5 ml soft agar culture media) was plated in each cell culture dish. Cells were harvested by trypsinization at ~80% confluence, mixed into top agar (10,000 cells/plate; 0.3% noble agar in soft agar culture media) and poured onto prepared plates. Cysmethynil or DMSO was included at the indicated concentrations in both the top and bottom agar layers. For each condition, triplicate samples (each consisting of three plates) were prepared. Plates were fed twice a week with 300 µl 1×MEM containing 10% FBS and the appropriate concentrations of cysmethynil or DMSO. After three weeks, plates were stained by addition of 300 µl of 10 mg/ml methylthiazoletetrazolium (MTT; Sigma-Aldrich, St. Louis Mo.) in PBS followed by incubation at 37° C. in an incubator with 5% $CO_2$ for three hours. Plates were then treated with 0.4N HCl in 300 µl isopropanol and incubated overnight prior to imaging.

Results

Identification of an Indole-Based Selective Inhibitor of Icmt

To identify novel small molecule inhibitors of Icmt, a diverse chemical library of ~10,000 compounds was screened. The library contained 70+ subfamilies derived from unique scaffolds. An in vitro screen was employed in which Icmt activity was measured as the incorporation of a $^3$H-methyl group into a farnesylated, Rce1-proteolyzed, K-Ras substrate in a coupled reaction. Compounds that showed >50% inhibition at 50 μM were subjected to a secondary screen using a newly developed small-molecule substrate of Icmt, biotin-S-farnesyl-L-cysteine (BFC). From this screen, a group of compounds with an indole core structure was identified that had significant activity against Icmt. The most potent of these compounds (see below) was 2-[5-(3-methylphenyl)-1-octyl-1H-indol-3-yl]acetamide (FIG. 1A), hereafter termed cysmethynil. This compound was independently synthesized and characterized to confirm identity and purity (see Example 2), and all studies described below were performed using the independently synthesized compound.

In the initial in vitro assay using BFC as the prenylcysteine substrate, the $IC_{50}$ for Icmt inhibition by cysmethynil was determined to be 2.4 μM (FIG. 1B). In this assay, the substrates and the inhibitor were premixed, and the reaction was initiated by the addition of enzyme. However, when the enzyme was premixed with inhibitor and AdoMet for 15 min prior to initiation of the reaction with BFC, a dramatic increase in inhibitor potency was observed with a measured $IC_{50}$ of <200 nM (FIG. 1B). These data suggest that cysmethynil is a time-dependent inhibitor of Icmt. Importantly, even at concentrations up to 50 μM, cysmethynil did not inhibit the other enzymes in the prenylation pathway (FTase, GGTase-I, Rce1 protease) nor did it inhibit an AdoMet-dependent DNA methyltransferase (SssI DNA methyltransferase) (results not shown).

Cysmethynil Treatment Impacts Cell Growth in an Icmt-Dependent Fashion.

Figure 2:
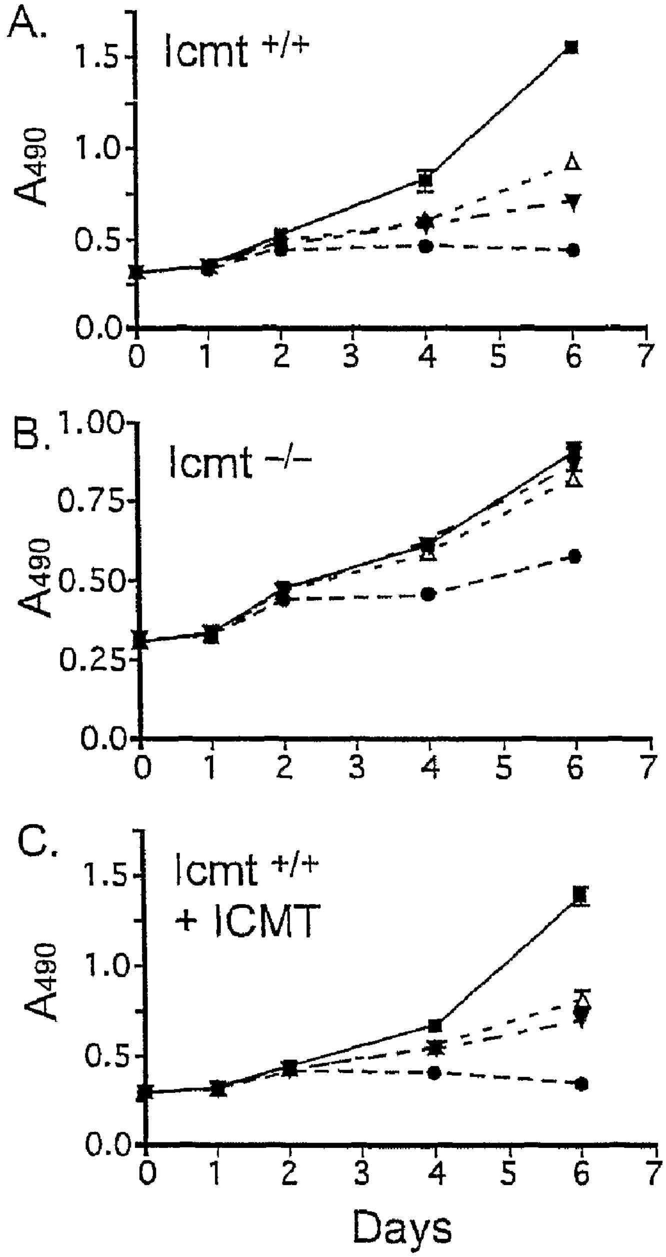
FIGS. 2A-2C. Icmt-dependent growth inhibition of mouse embryonic fibroblasts by cysmethynil. Mouse embryonic fibroblasts grown in media containing 10% serum were treated with DMSO (■) or cysmethynil at concentrations of 15 μM (Δ), 20 μM (▼) or 30 μM (●). Media and drug were replaced daily, and cell growth was monitored for six days. Data represent the mean and standard deviation of four replicate wells.

To evaluate the potential cellular activity of cysmethynil, advantage was taken of a cell model of Icmt deficiency developed from the gene disruption studies (Bergo et al, J. Biol. Chem. 276:5841-5845 (2001)). Reasoning that cells that had adapted to grow in the absence of Icmt activity should be resistant to the effects of the inhibitor, $Icmt^{-/-}$ mouse embryonic fibroblasts and matched wild-type cells were treated with increasing concentrations of the compound and cell growth was monitored out to 6 days of exposure (FIG. 2). Treatment with cysmethynil resulted in a dose-dependent inhibition of growth wild type cells (FIG. 2A), but $Icmt^{-/-}$ cells were largely unaffected by this treatment (FIG. 2B). Furthermore, when the human ICMT gene was stably expressed in $Icmt^{-/-}$ cells, the reconstituted cell line regained sensitivity to cysmethynil (FIG. 2C). These results provide strong evidence for an antiproliferative activity of cysmethynil that is mechanism-based, i.e. directly due to an impact on Icmt activity.

Cysmethynil Treatment of Cells Results in Mislocalization of Ras and Impairment of Growth Factor Signaling.

Figure 3:
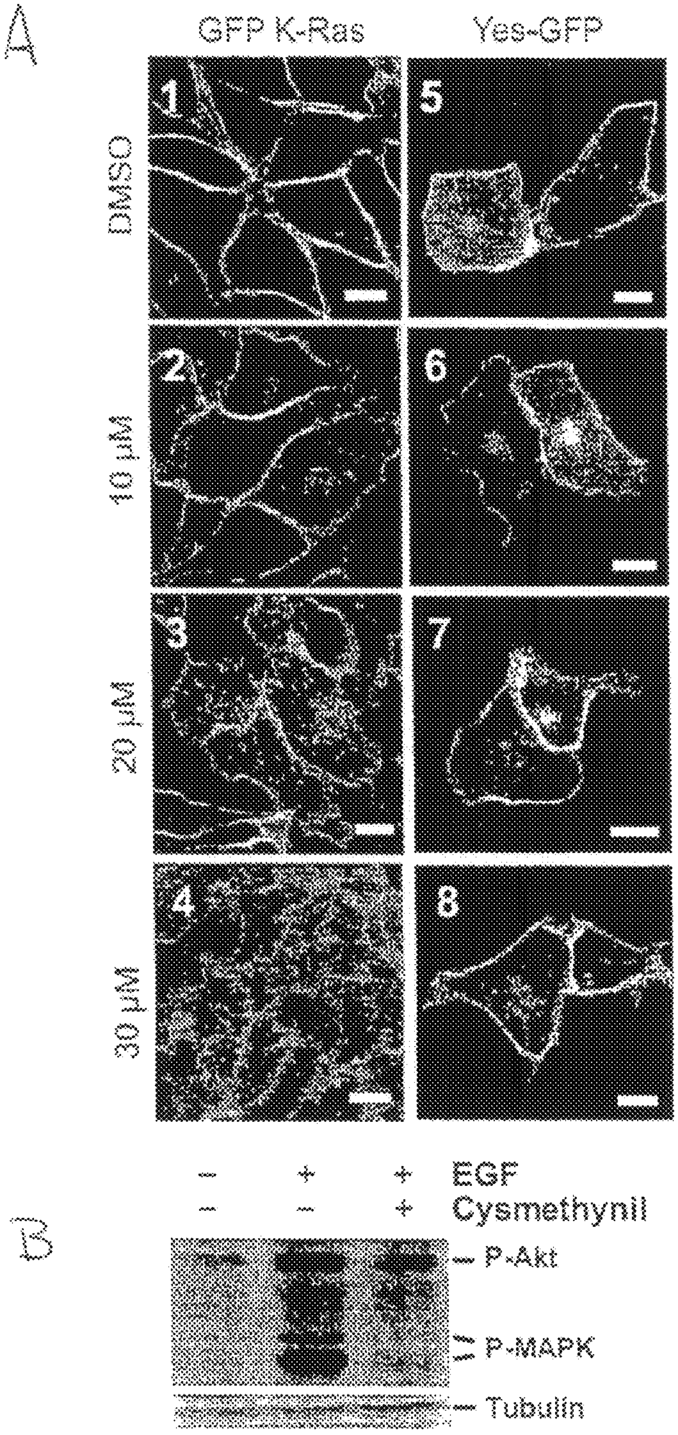
FIGS. 3A and 3B. Impact of cysmethynil treatment on Ras localization and signaling.

Carboxylmethylation is important for proper plasma membrane localization of Ras (Bergo et al, J. Biol. Chem. 275: 17605-17610 (2000)). Based on this observation, it was predicted that treatment of cells with an Icmt inhibitor would lead to a loss of Ras from the plasma membrane. To test this hypothesis, MDCK cells stably expressing GFP-tagged K-Ras were treated with increasing concentrations of cysmethynil for 72 h prior to imaging by confocal fluorescence microscopy. As shown in FIG. 3 (panels 1-4), cysmethynil treatment led to a dose-dependent mislocalization of GFP-K-Ras. Similar effects were noted for GFP-H-Ras and GFP-N-Ras in these cells and for all three Ras isoforms expressed in mouse embryonic fibroblasts (data not shown). As a control, MDCK cells expressing a C-terminal GFP fusion of Yes, a protein kinase localized to the plasma membrane by N-terminal myristoylation and palmitoylation (McCabe and Berthiaume, Mol. Biol. Cell 10:3771-3786 (1999)), were treated under the same conditions. Cysmethynil treatment did not affect the plasma membrane localization of Yes-GFP (FIG. 3, panels 5-8), indicating that the compound does not globally disrupt trafficking to the plasma membrane.

Growth factor signaling to MAPK involves CaaX proteins, again most notably Ras, and inhibition of CaaX protein methylation has been reported to impair epidermal growth factor (EGF)-mediated phosphorylation and activation of MAPK (Chiu et al, J. Biol. Chem. 279:7346 (2004), Winter-Vann et al, Proc. Natl. Acad. Sci. USA 100:6529-6534 (2003)). To evaluate the effect of cysmethynil treatment on EGF-mediated activation of MAPK and other signaling proteins, DKOB8 colon cancer cells were grown under low serum (1%) conditions in the presence of either vehicle or 1 μM cysmethynil. Following three days of treatment, the cells were treated with either EGF or additional vehicle. Lysates from the cells were separated on SDS-PAGE and immunoblotted with a mixture of phospho-specific antibodies for Akt and p42/44 MAPK, or with an antibody for β-tubulin. As shown in FIG. 3B, the level of activated Akt increased roughly 3-fold, and that of activated p42/44 MAPK nearly 10-fold in EGF-treated cells. The EGF-induced increase in MAPK was almost completely blocked by the cysmethynil treatment, while the increase in Akt phosphorylation was partially but not completely attenuated. This observation supports the hypothesis that cysmethynil treatment impacts on signaling through Ras-dependent pathways, as the activation of MAPK by EGF occurs primarily via the Ras pathway; corresponding activation of Akt involves both Ras-independent and Ras-dependent processes (Gschwind et al, Nat. Rev. Cancer 4:361-370 (2004)). Also, it is interesting to note that under low (1%) serum conditions, cysmethynil affects cellular processes at 5- to 10-fold lower concentrations than when the cells are grown in higher (8-10%) serum, suggesting that this compound, like many pharmacological agents, is buffered by serum.

Figure 4:
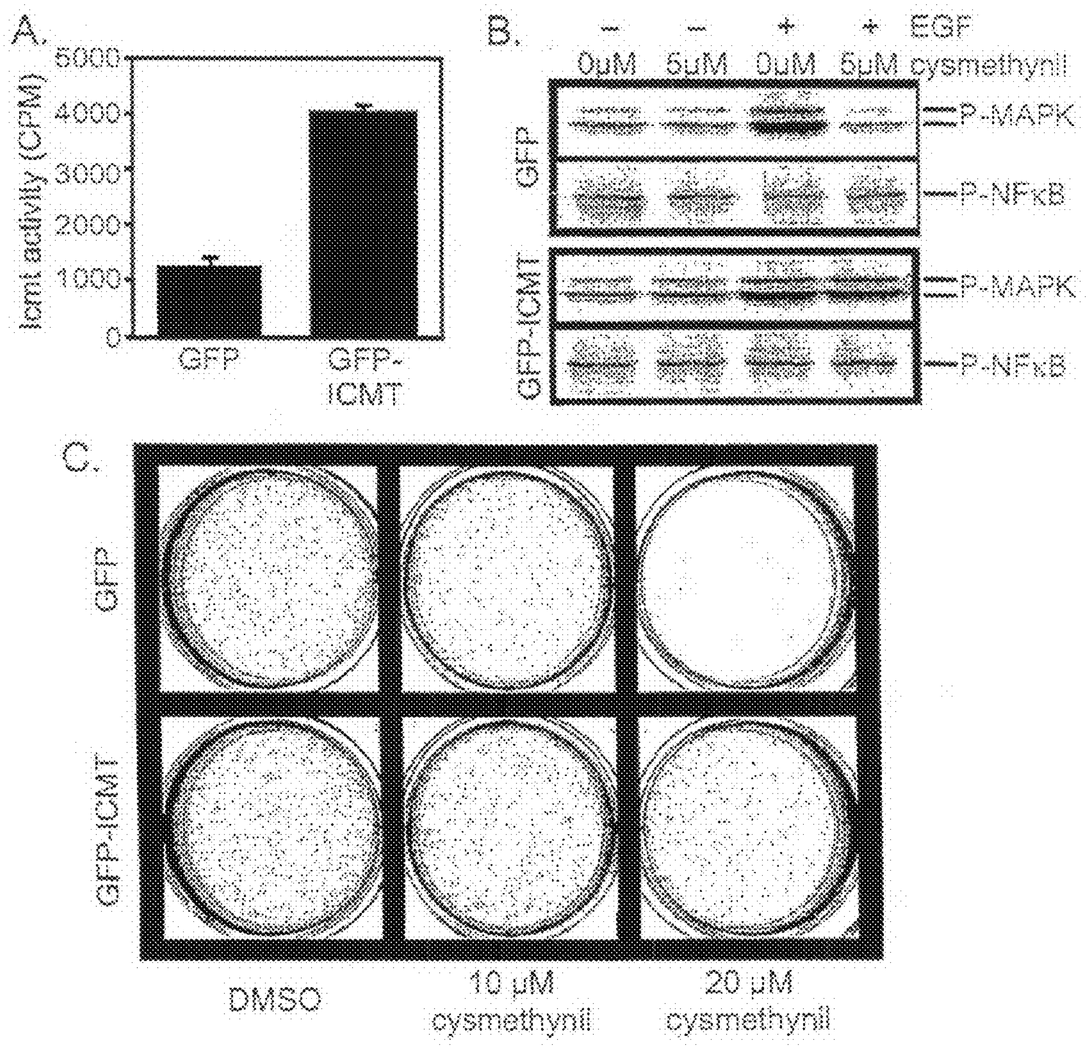
FIGS. 4A-4C. Overexpression of Icmt rescues EGF-stimulated MAPK activation and anchorage-independent growth in cysmethynil-treated cells.

Impact of Cysmethynil Treatment on the Transformed Phenotype of Colon Cancer Cells The data detailed above all point to a potential impact of Icmt inhibition on blocking the transformed phenotype of cancer cells. One of the classic methods to assess transformation of cells is by measuring their ability to grow in soft agar (Clark et al, Methods Enzymol. 255:395-412 (1995)), and genetic disruption of Icmt in cells has been shown to block mouse anchorage independent growth triggered by activated Ras (Bergo et al, J. Clin. Invest. 113:539-550 (2004)). In order to directly assess the role of Icmt in any ability of cysmethynil to block the transformed phenotype of cancer cells, the DKOB8 colon cancer cells were engineered to stably overexpress Icmt; conferring resistance to a pharmacological agent by overexpression of the target is a classic means to confirm the mechanism of action of the agent. Through this approach, it was possible to create a line of DKOB8 cells expressing GFP-Icmt in which the level of Icmt activity was elevated 4-fold compared to a parallel line in which GFP alone was expressed (FIG. 4A). Although modest, this level of Icmt overexpression was sufficient to protect the cells from cysmethynil blockade of EGF-stimulated MAPK activation (FIG. 4B), providing further confirmation that this effect of the inhibitor is due to its ability to impact on Icmt activity in the cells.

Having established that overexpression of Icmt conferred resistance to cysmethynil, both cell lines were then evaluated for the effect of cysmethynil on anchorage-independent growth. DKOB8/GFP and DKOB8/GFP-Icmt cells growing in soft agar were treated with either vehicle or increasing concentrations of cysmethynil. After three weeks, the plates were stained with MTT to identify viable cells and imaged. As shown in FIG. 4C, treatment with cysmethynil significantly impaired the ability of the DKOB8/GFP cells to grow in soft agar, with a concentration of 20 μM dramatically reducing the ability of cells to form colonies. However, elevated Icmt activity was sufficient to rescue the ability of the cells to form colonies in soft agar in the presence of 20 μM cysmethynil (FIG. 4C, lower wells). These results provide compelling evidence that cysmethynil blockade of Icmt is responsible for the ability of the compound to impact on both growth factor signaling pathways and on anchorage-independent growth of these cancer cells.

Summarizing, the functional consequence of carboxylmethylation of CaaX proteins has been a matter of speculation since the prenylation pathway was first identified (Clarke et al, Proc. Natl. Acad. Sci. USA 85:4643-4637 (1988), Hrycyna et al, EMBO J. 10:1699-1709 (1991)). Icmt-catalyzed methylation is clearly essential for some biologies, as evidenced by the embryonic lethal phenotype when the gene encoding this enzyme is disrupted in mice (Bergo et al, J. Biol. Chem. 276:5841-5845 (2001)). However, the contribution of carboxylmethylation to specific biological processes has been difficult to address. Although much work has been done using prenylcysteine analogs or agents that elevate AdoHcy to inhibit Icmt activity in cells (Winter-Vann et al, Proc. Natl. Acad. Sci. USA 100(11):6529-6534 (2003), Kramer et al, Mol. Biol. Cell 14:848-857 (2003), Lu et al, Circ. Res. 94:306-315 (2004), Roullet et al, J. Clin. Invest. 97:2384-2390 (1996), Kowluru et al, J. Clin. Invest. 98:540-555 (1996)), the non-specific nature of these compounds has made it difficult to attribute specific outcomes to an inhibition of Icmt (Ma et al, Biochemistry 33:5414-5420 (1994), Scheer and Gierschik, FEBS Lett. 319:110-114 (1993)). The establishment of cell lines lacking Icmt has greatly helped the field (Bergo et al, J. Clin. Invest. 113:539-550 (2004), Maske et al, J. Cell Biol. 162:1223-1232 (2003)), but researchers are restricted to these few cell lines.

Even with these limitations, there are exciting hints about the involvement of Icmt in a number of biological systems. An increasing body of evidence suggests that Icmt-catalyzed methylation impacts signaling through Ras and, more importantly, that a lack of Icmt can slow or even stop cellular transformation (Bergo et al, J. Clin. Invest. 113:539-550 (2004), Chiu et al, J. Biol. Chem. 279:7346 (2004), Winter-Vann et al, Proc. Natl. Acad. Sci. USA 100:6529-6534 (2003)). In addition, several studies have linked Icmt inhibition to significant effects on endothelial cells, including increased permeability and apoptosis (Kramer et al, Mol. Biol. Cell 14:848-857 (2003), (Wang et al, J. Biol. Chem. 272:25380-25385 (1997)) (Lu et al, Circ. Res. 94:306-315 (2004)). Inhibitors of Icmt might therefore have significant utility as anti-cancer agents. In fact, there is evidence that one existing anti-cancer drug, methotrexate, targets Icmt through an elevation of its product inhibitor AdoHcy (Winter-Vann et al, Proc. Natl. Acad. Sci. USA 100:6529-6534 (2003)).

Although much of the work on Icmt has centered on the consequences of carboxylmethylation of Ras proteins, some intriguing findings have been reported for other CaaX proteins processed by Icmt. Carboxylmethylation of RhoA plays a major role in stability of the protein (Bergo et al, J. Clin. Invest. 113:539-550 (2004), Backlund, J. Biol. Chem. 272: 33175-33180 (1997)), and the effects of Icmt inhibition on endothelial cells noted above has been suggested to be due to impact on carboxylmethylation of RhoA in these cells (Kramer et al, Mol. Biol. Cell 14:848-857 (2003), Lu et al, Circ. Res. 94:306-315 (2004)). Outside the family of GTPases, carboxylmethylation of lamin B clearly influences its interaction with the nuclear envelope (Maske et al, J. Cell Biol. 162:1223-1232 (2003)). The identification of cysmethynil as a potent inhibitor of Icmt detailed here provides a new and selective pharmacological tool to probe these potential functional consequences of CaaX protein methylation in cellular systems and also the involvement of Icmt in biologies important in both normal and pathological cellular processes.

Example 2

Synthesis and Characterization of Cysmethynil

Figure 5:
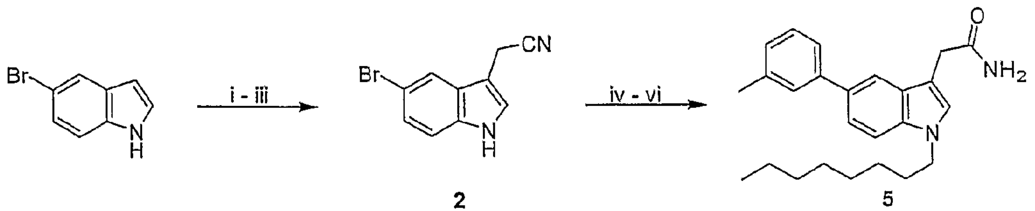
FIG. 5. Summary of the synthesis of 2-[5-(3-methylphenyl)-1-octyl-1H-indol-3-yl]acetamide (Cysmethylnil). Reagents and conditions: (i) 37% aq. $CH_2O$, 40% aq. $(CH_3)_2NH$, 1,4-dioxane, 17M HOAc, 94%. (ii) $(CH_3)_2SO_4$, THF, 100%. (iii) KCN aq. 90%. (iv) powdered KOH, t-BuOH, reflux 90 min., 81%. (v) 3-Methylbenzeneboronic acid, $Pd(PPh_3)_4$ (6 mol %), toluene, abs. EtOH, $NaHCO_3$ aq., reflux 18 h, 50%. (vi) NaH (60% dispersion), 1-bromooctane, DMF, rt 18 h, 81%.

The details of the synthesis of 2-[5-(3-methylphenyl)-1-octyl-1H-indol-3-yl]acetamide (Cysmethynil) are provided below (see FIG. 5 for a summary of the synthesis:

N-[(5-bromo-1H-indol-3-yl)methyl]-N,N-dimethylamine (1). A 1000 ml three-necked round bottom flask equipped with a thermometer, magnetic stir bar and a dropping addition funnel was charged sequentially with 1,4-dioxane (52 ml), 17 M acetic acid (52 ml), 37% wt. aqueous formaldehyde (4.0 ml, 5.4 mmol), and $H_2O$ (4.0 ml). The flask was immersed in a NaCl/ice bath and 40% wt. aqueous dimethyl amine (7.1 ml, 56 mmol) was added at once with stirring. To this cooled solution was added a solution of 5-bromoindole (10.0 g, 51.0 mmol) in 1,4-dioxane (52 ml) at a rate such that the reaction temperature did not exceed 0° C. Stirring was continued for 2 h after which time the reaction mixture was removed from the ice bath and allowed to stir overnight (12 h) at room temperature. The reaction mixture was diluted with $H_2O$ (640 ml) then charcoal (~3 g) and Celite (~3 g) were added. The mixture was stirred 10 min and then filtered. To the filtrate was added 2 M NaOH (500 ml) with stirring. The resulting precipitate was filtered under vacuum and the filter cake washed with water (3×200 ml). The collected solid was dried overnight under vacuum to give a white powder (12.65 g, 98%). Recrystallization from i-PrOH gave colorless crystals (12.13 g, 94%) M.P. 149-152° C. $^1$H NMR δ 8.54 (bs, 1H), 7.83-7.82 (m, 1H), 7.25 (dd, 1H, J=8.24 Hz, J=1.92 Hz), 7.17 (dd, 1H, J=8.79 Hz, J=0.55 Hz), 7.06 (d, 2.27 Hz), 3.57 (s, 2H), 2.70 (s, 6H); $^{13}$C NMR δ 134.8, 129.6, 124.8, 124.7, 121.9, 113.1, 112.8, 112.5, 54.4, 45.3; IR (thin film, $CHCl_3$, $cm^{-1}$) 3429, 3104, 2995, 2818, 2589, 1450; FAB MS m/z 253.12 ($M^+$); Anal. Calcd. for $C_{11}H_{13}BrN_2$: C, 52.19; H, 5.18; N, 11.07. Found: C, 52.25; H, 5.24; N, 11.10.

(5-bromo-1H-indol-3-yl)acetonitrile (2). Under an atmosphere of argon, a solution of 1 (9.00 g, 36.0 mmol) and 17 M acetic acid (0.54 ml, 9.18 mmol) in anhydrous THF (50 ml), was added dropwise with stirring over 40 minutes to a solution of dimethyl sulfate (17.5 ml, 180 mmol) and 17 M acetic acid (0.54 ml, 9.18 mmol) in anhydrous THF (20 ml). During the addition, the reaction temperature was kept between 10-15° C. Stirring was continued for 1 h, after which time a white solid was filtered off under vacuum. The filter cake was washed with $Et_2O$ (200 ml) and air dried for 1 h. The collected white powder (13.02 g, 100%) was dissolved with vigorous stirring in water (70 ml) containing KCN (6.94 g, 106 mmol). The solution was then heated on an oil bath at 60-70° C. (internal) for 1 h. After cooling to room temperature, the reaction mixture was extracted with $Et_2O$ (2×150 ml). The combined organic extracts were washed with saturated aqueous $NaHCO_3$ (100 ml), saturated aqueous NaCl (2×100 ml) and dried ($Na_2SO_4$). The drying agent was removed by filtration and the filtrate was concentrated under reduced pressure to give a pale solid that was recrystallized from $CCl_4$ to give the desired nitrile as pale micro needles (7.62 g, 90% from 1). M.P. 100-102° C. (Juby and Hudyma, *J. Med. Chem.* 12:

3396-3401 (1969)) 102.5-104° C.). $^1$H NMR δ 8.23 (bs, 1H), 7.72-7.70 (m, 1H), 7.35-7.22 (m, 3H), 3.79 (s, 2H); $^{13}$C NMR δ 134.8, 127.7, 125.8, 124.0, 120.7, 117.8, 113.5, 113.0, 104.4, 14.3; IR (thin film, $CHCl_3$, $cm^{-1}$) 3423, 2361, 2253, 1569, 1461; FAB MS m/z 236.1 ($MH^+$); Anal. Calcd. for $C_{10}H_7BrN_2$: C, 51.09; H, 3.00; N, 11.92. Found: C, 51.07; H, 3.03; N, 11.87.

2-(5-bromo-1H-indol-3-yl)acetamide (3). Nitrile 2 (1.74 g, 7.40 mmol), was refluxed in t-BuOH (15 ml) containing finely powdered 85% KOH (3.91 g, 59 mmol) for 1.5 h. The reaction mixture was cooled to room temperature, diluted with water (15 ml) and acidified with 1 N HCl (59 ml). The resulting suspension was filtered at the vacuum and filter cake was washed with water (20 ml) then dried in vacuo over $CaCl_2$ for three days. The product was isolated as an off-white solid (1.51 g, 81%). $^1$H NMR (300 MHz, DMSO-$d_6$) δ 11.09 (s, 1H), 7.74 (m, 1H), 7.39-7.16 (m, 3H), 6.86 (s, 1H), 3.44 (s, 2H); $^{13}$C NMR (75 MHz, DMSO-$d_6$) δ 172.6, 134.8, 129.1, 125.5, 123.3, 121.1, 113.3, 111.0, 109.0, 32.3; IR (thin film, $CHCl_3$, $cm^{-1}$) 3416, 2954, 2923, 2853, 1657; 1460 FAB MS m/z 253.1 ($M^+$); Anal. Calcd. for $C_{10}H_9BrN_2O$: C, 47.46; H, 3.58; 0, 6.32; N, 11.07. Found: C, 48.37; H, 3.88; 0, 6.29; N, 10.45.

2-(5-phenyl-1H-indol-3-yl)acetamide (4). To a suspension of bromoindole 3 (1.31 g, 5.19 mmol) in anhydrous toluene (103 ml) was added $Pd(PPh_3)_4$ (0.34 g, 5.7 mol %). The suspension was stirred at room temperature for 1 h. To the resulting bright yellow suspension was added in one portion a solution of 3-methylbenzeneboronic acid (1.11 g, 7.8 mmol, 1.5 equiv) in anhydrous EtOH (31 ml) followed immediately by a saturated aqueous solution of $NaHCO_3$ (51 ml). After refluxing for 18 h, the biphasic mixture was cooled to room temperature and then poured into a solution of saturated aqueous NaCl (100 ml). The organic phase was separated and the aqueous phase was extracted with EtOAc (3×100 ml). Organic extracts were combined and dried ($Na_2SO_4$). The drying agent was removed by filtration and the filtrate was concentrated under reduced pressure to give a thick amber oil. Flash column chromatography (silica gel, 100% DCM <MeOH:DCM (1:10)) gave 4 as a tan colored solid (0.686 g, 50%). $^1$H NMR δ 8.19 (bs, 1H), 7.78 (s, 1H), 7.52-7.13 (m, 7H), 5.65 (bs, 1H), 5.31 (bs, 1H), 3.79 (s, 2H), 2.44 (s, 3H); $^{13}$C NMR δ 174.1, 142.0, 138.3, 135.8, 134.0, 128.6, 128.2, 127.4, 124.5, 124.2, 122.6, 117.1, 111.6, 109.6, 33.0, 21.6; IR (thin film, $CHCl_3$, $cm^{-1}$) 3410, 3324, 3194, 3053, 2918, 1660, 1604, 1466; ESI m/z 265.3 ($MH^+$); Anal. Calcd. for $C_{17}H_{16}N_2O$: C, 77.25; H, 6.10; 0, 6.05; N, 10.60. Found: C, 75.95; H, 6.05; 0, 6.24; N, 9.76.

2-[5-(3-methylphenyl)-1-octyl-1H-indol-3-yl]acetamide (Cysmethynil; 5). To a stirred suspension of NaH (60% dispersion in mineral oil, 0.092 g, 2.3 mmol, washed with 2×3 ml dry pentane) in anhydrous DMF (5 ml) at room temperature was added a solution of indole 4 (0.500 g, 1.89 mmol) in anhydrous DMF (8.4 ml) dropwise over ten min. After stirring at room temperature for 1.5 h, following which 1-bromooctane (1.0 ml, 1.12 g, 5.79 mmol) was added dropwise over 5 minutes. After being heated on an oil bath at 53-58° C. for 18 h, the reaction mixture was cooled to room temperature and poured into ice water (80 ml). The suspension was stirred 10 min and extracted with $Et_2O$ (6×25 ml). The organic extracts were combined, washed with brine (4×25 ml) and dried ($Na_2SO_4$). The drying agent was removed by filtration and the filtrate was concentrated under reduced pressure to give an amber oil. Flash column chromatography (silica gel, 100% DCM→MeOH:$CH_3CN$ (1:10)) gave 5 as a viscous amber oil (0.576 g, 81%). $^1$H NMR δ 7.75 (s, 1H), 7.49-7.30 (m, 5H), 7.13 (d, 1H, J=7.14 Hz), 7.08 (s, 1H), 5.68 (bs, 1H), 5.36 (bs, 1H), 4.11 (t, 2H, J=7.14 Hz), 3.77 (s, 2H), 2.44 (s, 3H), 1.86 (m, 2H), 1.33-1.27 (m, 10H) 0.88 (t, 3H, J=6.59 Hz); $^{13}$C NMR δ 174.2, 142.1, 138.3, 137.1, 136.0, 133.4, 128.6, 128.1, 127.8, 127.3, 124.5, 122.0, 117.3, 110.0, 108.0, 46.5, 33.3, 33.0, 31.8, 30.3, 29.1, 27.0, 22.6, 21.6, 14.1; IR (thin film, $CHCl_3$, $cm^{-1}$) 3461, 3338, 3194, 2927, 1668, 1605, 1475, 1373; HRMS (FAB) calcd. for $C_{25}H_{32}N_2O$ ($M^+$) 376.5345, found 376.5140.

NMR spectra were obtained at 300 MHz for $^1$H and 75 MHz for $^{13}$C unless otherwise specified. Chemical shifts are reported in ppm (δ) relative to TMS. IR spectra were recorded on a Nicolet Avatar 360 FT IR spectrometer. FAB mass spectra were obtained on a JEOL JMS SX-102 high resolution mass spectrometer. Elemental analyses were performed by Atlantic Microlabs (Norcross Ga.). Tetrahydrofuran (THF) was refluxed and distilled under argon from sodium/benzophenone immediately prior to use. Toluene was distilled under argon from $CaH_2$ immediately prior to use. Absolute ethanol was refluxed and distilled under argon from magnesium turnings. Tetrakistriphenylphosphine palladium(0) and 3-methylbenzeneboronic acid were purchased from Strem Chemical and used without further purification. All other reagents and solvents were used as received from Aldrich Chemical Company.

Example 3

Assay for Recombinant Human Icmt

Experimental Details

Materials. Streptavidin-sepharose beads were purchased from Amersham, trans,trans-farnesyl bromide, biotin N-hydroxysuccinimide ester and S-(5'-adenosyl)-L-methionine p-toluenesulfonate were purchased from Sigma-Aldrich, L-cysteine was purchased from Novabiochem, [$^3$H-methyl]-S-adenosyl-L-methionine was purchased from Perkin Elmer Life Sciences, farnesylthioacetic acid (FTA) was purchased from Biomol, S-(5'-adenosyl)-L-homocysteine was purchased from Fluka. The N-acetyl-5-farnesylcysteine methyl ester (AFCME) and N-acetyl-5-farnesylcysteine methyl amide (AFCMA) were synthesized as previously described (Zhang et al, J. Biol. Chem. 269(23): 15973-15976 (1994), Bodansky, The practice of peptide synthesis, New York: Springer-Verlag (1984), Brown et al, J. Biol. Chem. 269: 15973-15976 (1994)). Recombinant human Icmt was prepared by infection of Sf9 cells with a recombinant baculovirus containing the entire open reading frame of the human Icmt cDNA as described (Winter-Vann et al, Proc. Natl. Acad. Sci. USA 100(11):6529-6534 (2003)). The membrane fraction of the infected Sf9 cells, isolated as described for studies with the Rce1 protease (Otto et al, J. Biol. Chem. 274(13): 8379-8382 (1999)), was used as the source of Icmt for all studies described.

Syntheses of biotin-S-farnesyl L-cysteine (BFC). S-Farnesyl L-cysteine (FC) was prepared by reaction of farnesyl bromide with L-cysteine in methanol/ammoniac solvent as described (Brown et al, J. Biol. Chem. 269:15973-15976 (1994)). The resultant FC product was separated from L-cysteine by extraction with butanol/$H_2O$ (1:1); the butanol phase was then evaporated under reduce pressure and the FC product washed several times with hexane to remove residual farnesyl bromide.

Two coupling procedures were used to attach the biotin moiety to the amino group of FC; both involved the use of biotin N-hydroxysuccinimide methylester (biotin-NHS) as the biotinylation agent. In the first method, an excess of biotin-NHS (75 μmol) to FC (7.5 μmol) was used. The two compounds were dissolved in 2.3 ml of DMSO and 200 μl of 1M Hepes, pH 12, was added. Following a 2 h incubation at room temperature, the DMSO was evaporated under reduced pressure and the resulting residue extracted with a solution of butanol/$H_2O$ (1:1). The butanol phase was dried and the residue dissolved in 100 μl of methanol; this solution was then diluted to 1 ml by addition of 0.1% trifluoroacetic acid (TFA). The addition of the TFA resulted in the appearance of a white precipitate of essentially pure BFC as judged by chromatography and NMR analysis.

The second coupling method used an excess of FC (2.5 mmol) compared to biotin-NHS (0.73 mmol); these two compounds were dissolved in 18 ml of DMSO. To this solution was added 2 ml of 1M Hepes, pH 12, and the coupling allowed to proceed for 2 h at room temperature. As with the first method, the DMSO was evaporated under reduced pressure, the resulting residue extracted with a solution of butanol/$H_2O$ (1:1), and the butanol phase dried and the residue dissolved in methanol. Because of the excess of FC present with the BFC product, specific precipitation of the BFC product was unsuccessful. Instead, the BFC was purified by preparative HPLC on a $C_{18}$ column developed in $CH_3CN$/$H_2O$ (2:3). On this matrix, BFC was well-resolved from FC. The peak fractions were collected and solvent evaporated under reduced pressure; the resulting product was white solid that was >95% pure as judged by analytical reverse-phase HPLC $C_{18}$ matrix developed in $CH_3CN$/$H_2O$/TFA (90:10:0.1). Proton NMR spectra of the products obtained by either method were completely consistent with that expected for authentic BFC.

Icmt assay. The assay developed for Icmt activity involved quantitation of [$^3$H]methyl incorporation into the small molecule substrate BFC. For the standard assay, reactions were initiated by addition of Sf9 membranes containing Icmt (0.5 μg protein) to an assay mixture containing BFC (4 μM) and [$^3$H]AdoMet (5 μM, 1.3 Ci/mmol) in 100 mM Hepes, pH 7.4 and 5 mM $MgCl_2$ in a total volume of 45 μl. Reactions were carried out for 20 min at 37° C., whereupon they were terminated by addition of 5 μl of 10% Tween 20. Following termination, streptavidin beads (10 μl of packed beads suspended in 500 μl of 20 mM $NaH_2PO_4$, pH 7.4, containing 150 mM NaCl) were added, and the mixtures mixed by gentle agitation overnight at 4° C. The beads were harvested by centrifugation in a tabletop microcentrifuge at 10,000 rpm for 5 min and washed 3 times with 500 μl of 20 mM $NaH_2PO_4$, pH 7.4, containing 150 mM NaCl. The beads were then suspended in 100 μl of the same buffer, transferred to scintillation vials, and radioactivity determined. For the kinetic analyses, the concentrations of substrates (AdoMet, BFC) or additional ligands (eg. AdoHcy, AFCME, etc) were varied.

Results

Characterization of the small molecule Icmt substrate, BFC. To overcome the inherent problems associated with use of S-prenylated peptides and proteins as Icmt substrates (expense in production, unwieldy separation techniques, etc), a small molecule substrate for the enzyme was synthesized that contains an appended biotin moiety (FIG. 6A) to facilitate the separation required for product analysis. The coupling of biotin moiety to the free amino group of the S-farnesylcysteine, FC, was readily achieved through the use of commercial biotin N-hydroxysuccinimide ester and the product BFC could be readily purified by precipitation or by reverse-phase chromatography. BFC was characterized in terms of its ability to serve as a substrate for recombinant human Icmt using a standard in vitro methylation assay (FIG. 6B). The apparent $K_m$ of BFC was 2.1±0.4 μM, which is essentially identical to the $K_m$ of 2.1 μM determined for farnesylated, Rce1-proteolyzed K-Ras (data not shown). Hence, BFC is a comparable to K-Ras as an Icmt substrate and has the added advantages of being a stable small molecule that can be readily captured on avidin resins.

Example 4

Criticality of Substituents on Indole Nitrogen of Icmt Inhibitors for Time-Dependent Inhibition A select set of the compounds of the invention have been examined to determine whether they exhibited time-dependent inhibition. The data resulting from this study demonstrate that the substituent on the indole nitrogen plays a significant role in this behavior. Compounds containing a variety of R1 substitutions on the indole nitrogen were assayed for inhibitory potential either under standard conditions or following pre-incubation with Icmt for 30 min at 37° C. When R1 was a small carbon chain, such as isobutyl or cyclopropyl, the compounds exhibited essentially the same $IC_{50}$ value with or without preincubation of the compound with the enzyme (Table 3). However, when the R1 substituent was a longer carbon chain or a more hydrophobic moiety, such as hexyl, octyl (to yield cysmethynil), benzyl, 3-trifluoromethyl benzyl or naphthyl, time-dependent inhibition was observed. Thus, a decrease in the length/hydrophobicity of the indole nitrogen substituent is accompanied by loss of the time-dependent properties of this indole-class of Icmt inhibitors.

TABLE 3

Indole nitrogen substituents influence manifestation of time-dependent inhibition of Icmt. The $IC_{50}$ values for inhibition of Icmt by the indicated indole compounds were determined with (PI) or without (No PI) pre-incubation of the enzyme with the compound prior to the initiation of the assay.

| | | | | |
|---|---|---|---|---|
| | | $IC_{50}$ | | |
| $R_1$ | 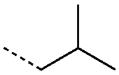 | 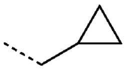 | 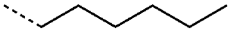 | 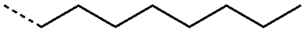 |

TABLE 3-continued

| | | | | |
|---|---|---|---|---|
| 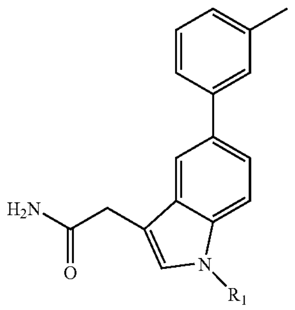 | 15.7 ± 2 μM<br>17.7 ± 4.7 μM | 9.1 ± 1.8 μM<br>9.5 ± 1.2 μM | 7.4 ± 0.4 μM<br>1.7 ± 0.08 μM | 2.1 ± 0.9 μM<br>0.29 ± 0.03 μM |
| | | $IC_{50}$ | | |
| $R_1$ | 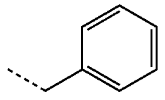 | 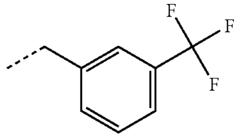 | 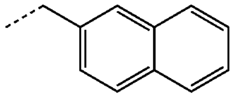 | |
| 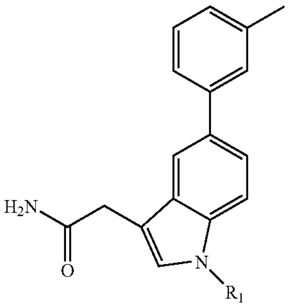 | 6.4 ± 2 μM<br>2.4 ± 0.7 μM | 8 ± 4.5 μM<br>0.71 ± 0.09 μM | 17.2 ± 4.3 μM<br>1.34 ± 0.2 μM | No PI<br>PI |

Example 5

Impact of Icmt Inhibition on Rho and Rac Function

The impact of Icmt inhibition on function of the geranylgeranylated GTPases Rho and Rac in cells has been examined. This study was carried out in MD-MBA-231 breast cancer cells. Tumorigenesis and metastatic behavior of these cells is dependent on high levels of Rho GTPases in particular. MDA-MB-231 cells were grown under standard conditions in DMEM/5% serum and treated on day zero with either the vehicle DMSO (−, D) or with 20 μM cysmethynil (+, Cys). Cells were harvested and lysates containing equal amounts of protein were resolved by SDS-PAGE and subjected to immunoblot analysis with specific antibodies to RhoA (FIG. 7A), or Rac1 (FIG. 7B). As a control, immunoblot analysis for α-tubulin was carried out on all samples.

The results of this analysis, shown in FIG. 7, demonstrate that cysmethynil treatment markedly reduces the steady-state levels of both Rho and Rac in the cells. Following a 6 day treatment of the cells with cysmethynil, Rho levels dropped to almost undetectable and Rac levels were reduced >80% as assessed by immunoblot analysis, while the level of a control protein, α-tubulin, was only marginally affected. These data indicate that inhibition of Icmt in cells leads to a marked decrease in function of both Rho and Rac GTPases, and thus underscore the potential utility of Icmt inhibition in treatment of pathophysiologies such as tumor cell metastasis and inflammation, that are dependent on a high level of activity of these proteins All documents and other information sources cited above are incorporated herein in their entirety by reference.

What is claimed is:

1. A compound of Formula I:

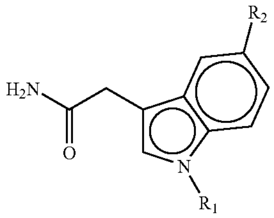

wherein $R_1$ is:

an alkyl, substituted or unsubstituted, a $(CH_2)_n$-substituted or unsubstituted aryl, n being an integer between 0 and 6, or a $(CH_2)_n$—O-substituted or unsubstituted aryl, n being an integer between 0 and 6, and wherein $R_2$ is a $(CH_2)_m$-substituted or unsubstituted aryl, m being an integer between 0 and 4; or pharmaceutically acceptable salt thereof.

2. The compound according to claim 1 wherein $R_1$ is:

a $C_1$-$C_{20}$ alkyl, substituted or unsubstituted, a —$(CH_2)_n$-phenyl or —$(CH_2)_n$-napthyl, substituted or unsubstituted, n being an integer between 1 and 4, or a —$(CH_2)_n$—O-phenyl or $(CH_2)_n$—O-napthyl, n being an integer between 1 and 4, and wherein $R_2$ is a $(CH_2)_m$-phenyl, wherein said phenyl is unsubstituted or substituted with at least one halogen, at least one unsubstituted or substituted alkyl or at least one —O—Y wherein Y is a $C_1$-$C_4$ alkyl or an aryl, m being an integer between 0 and 4; or pharmaceutically acceptable salt thereof.

3. A compound of Formula I:

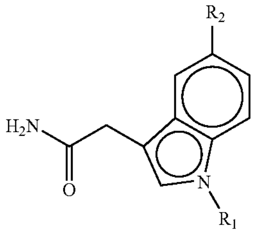

wherein $R_1$ is:

a linear, branched or cyclic $C_4$-$C_{15}$ alkyl, a $(CH_2)_n$-phenyl wherein said phenyl is unsubstituted or meta or para substituted with at least one branched $C_4$ unsubstituted alkyl or a $CX_3$, wherein X is a halogen, n being an integer between 1 and 4, or a $(CH_2)_n$—O-phenyl wherein said phenyl is unsubstituted or meta or para substituted with at least one branched $C_4$ unsubstituted alkyl or a $CX_3$, wherein X is a halogen, n being an integer between 1 and 4, and wherein $R_2$ is a $(CH_2)_m$-phenyl wherein said phenyl is unsubstituted or substituted with at least one halogen, at least one $CX_3$, wherein X is a halogen, or at least one —O—Y wherein Y is a $C_1$-$C_4$ alkyl or phenyl, substituted or unsubstituted, m being an integer between 0 and 4; or pharmaceutically acceptable salt thereof.

4. The compound according to claim 3 wherein said compound is selected from the group consisting of

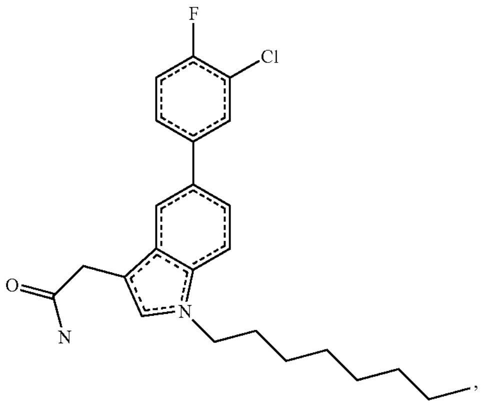
,

-continued

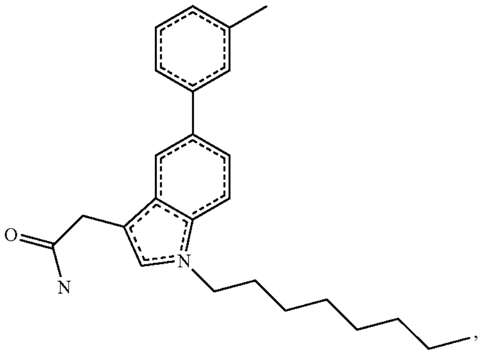
,

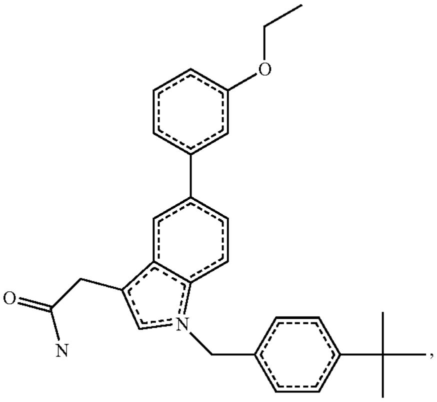
,

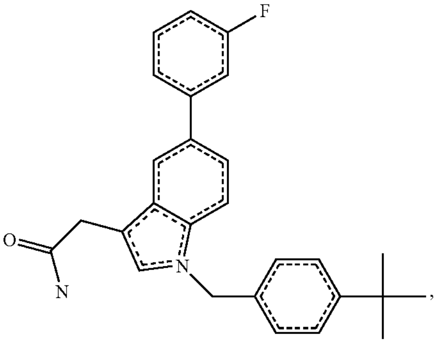
,

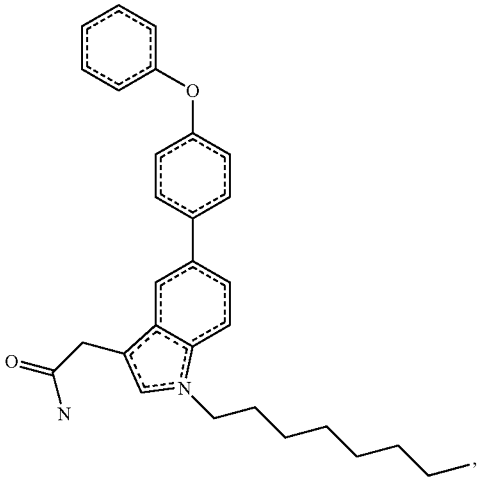
,

-continued

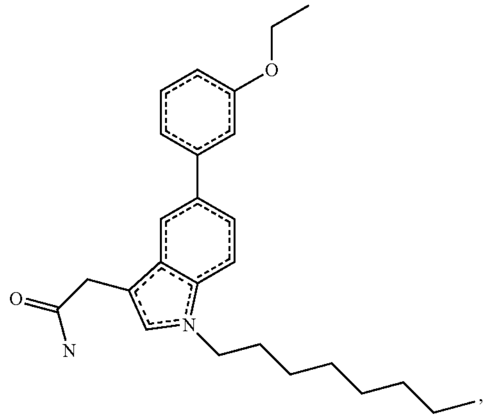

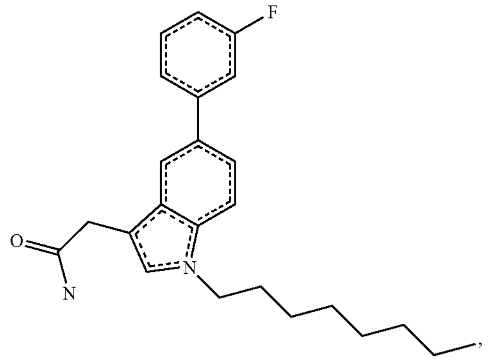

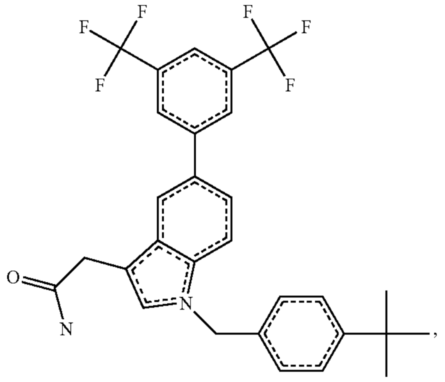

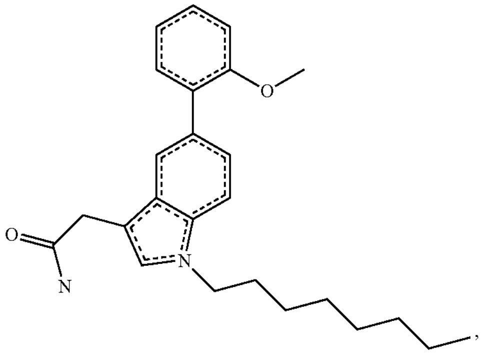

and

-continued

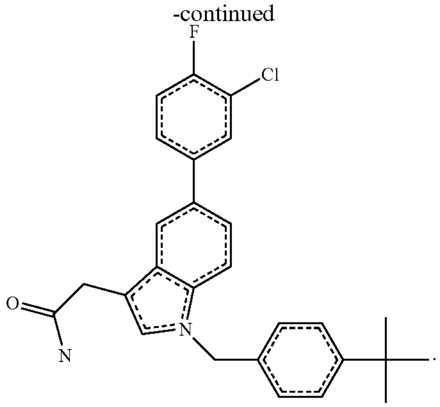

5. The compound according to claim 3 wherein said compound is

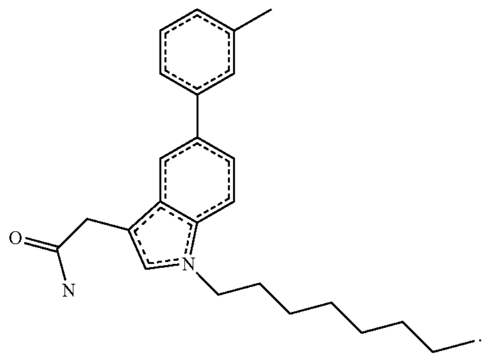

6. A pharmaceutical composition comprising the compound according to claim 1 and a pharmaceutically acceptable carrier.

7. The pharmaceutical composition according to claim 6 wherein said composition is in the form, of a sterile solution.

8. A pharmaceutical composition comprising the compound according to claim 3 and a pharmaceutically acceptable carrier.

9. A method of treating colo-rectal cancer comprising administering to a mammal in need thereof a compound of Formula I

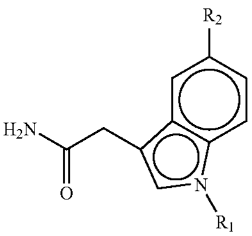

wherein $R_1$ is:

an alkyl, a $(CH_2)_n$-substituted or unsubstituted aryl, n being an integer between 0 and 6, or a $(CH_2)_n$—O-substituted or unsubstituted aryl, n being an integer between 0 and 6, and wherein $R_2$ is a $(CH_2)_m$-substituted or unsubstituted aryl, m being an integer between 0 and 4; or pharmaceutically acceptable salt thereof, in an amount sufficient to effect said treatment.

10. The method according to claim 9 wherein said mammal is a human.

11. A method of inhibiting Icmt-catalyzed CaaX protein methylation in a mammal comprising administering to a mammal in need thereof an amount of a compound of Formula I

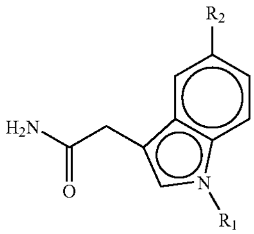

wherein $R_1$ is:

an alkyl, a $(CH_2)_n$-substituted or unsubstituted aryl, n being an integer between 0 and 6, or a $(CH_2)_n$—O-substituted or unsubstituted aryl, n being an integer between 0 and 6, and wherein $R_2$ is a $(CH_2)_m$-substituted or unsubstituted aryl, m being an integer between 0 and 4; or pharmaceutically acceptable salt thereof, in an amount sufficient to effect said inhibition.

12. The method according to claim 11 wherein said mammal is a human.

13. The method according to claim 11 wherein said mammal has colo-rectal cancer.

* * * * *